US010937529B2

(12) United States Patent
Azuma et al.

(10) Patent No.: US 10,937,529 B2
(45) Date of Patent: Mar. 2, 2021

(54) FAMILY TREE CONSTRUCTION SUPPORTING METHOD AND FAMILY TREE CONSTRUCTION SUPPORTING DEVICE

(71) Applicants: FUJITSU LIMITED, Kawasaki (JP); National Cancer Center, Tokyo (JP)

(72) Inventors: Mitsuhiro Azuma, Kawasaki (JP); Takuya Nagasawa, Kawasaki (JP); Michihiko Aki, Kawasaki (JP); Teruhiko Yoshida, Chuo (JP); Kokichi Sugano, Chuo (JP); Mineko Ushiama, Chuo (JP); Hiromi Sakamoto, Chuo (JP)

(73) Assignees: FUJITSU LIMITED, Kawasaki (JP); NATIONAL CANCER CENTER, Tokyo (JP)

( * ) Notice: Subject to any disclaimer, the term of this patent is extended or adjusted under 35 U.S.C. 154(b) by 371 days.

(21) Appl. No.: 15/703,281

(22) Filed: Sep. 13, 2017

(65) Prior Publication Data
US 2018/0101649 A1 Apr. 12, 2018

(30) Foreign Application Priority Data

Oct. 7, 2016 (JP) .............................. JP2016-199281

(51) Int. Cl.
*G06T 11/20* (2006.01)
*G16H 10/60* (2018.01)
(Continued)

(52) U.S. Cl.
CPC ............ *G16H 10/60* (2018.01); *G16H 20/00* (2018.01); *G16H 40/63* (2018.01); *G16H 50/20* (2018.01);
(Continued)

(58) Field of Classification Search
CPC ...... G06F 16/20; G06F 16/335; G06F 16/337; G06F 3/04817; G06F 16/43;
(Continued)

(56) References Cited

U.S. PATENT DOCUMENTS 10,347,360 B2 * 7/2019 Hyland ................. G16B 20/00
2002/0143578 A1 10/2002 Cole et al.
(Continued)

FOREIGN PATENT DOCUMENTS

JP 2002-503943 A 2/2002
JP 2005-049960 A 2/2005
(Continued)

OTHER PUBLICATIONS

Bennett et al., "Standardized Human Pedigree Nomenclature: Update and Assessment of the Recommendations of the National Society of Genetic Counselors", National Society of Genetic Counselors, Inc., vol. 17, pp. 424-433, 2008, cited in Specification. (10 pages).

(Continued)

*Primary Examiner* — Maroun P Kanaan
(74) *Attorney, Agent, or Firm* — Westerman, Hattori, Daniels & Adrian, LLP

(57) ABSTRACT

Provided is a non-transitory computer-readable storage medium storing a program causing a computer to execute a process, the process including: receiving a first operation that specifies a person symbol from a plurality of person symbols representing persons present in a family tree; displaying a plurality of first candidate person symbols capable of being connected with the person symbol specified by the received first operation by referring to a first storage unit that stores attribute information with respect to each of a plurality of persons; receiving a second operation that selects a first candidate person symbol from the plurality of first candidate person symbols that have been displayed; and
(Continued)

displaying the first candidate person symbol selected by the received second operation while the selected first candidate person symbol is being connected with the person symbol specified by the first operation.

20 Claims, 20 Drawing Sheets

(51) Int. Cl.
*G16H 50/20* (2018.01)
*G16H 20/00* (2018.01)
*G16H 40/63* (2018.01)
*G06F 3/0481* (2013.01)
*G06F 3/0482* (2013.01)

(52) U.S. Cl.
CPC ........ *G06F 3/0482* (2013.01); *G06F 3/04817* (2013.01)

(58) Field of Classification Search
CPC ..... G06F 16/953; G06F 3/0482; G16H 10/60; G16H 50/70; G06K 9/627
See application file for complete search history.

(56) References Cited

U.S. PATENT DOCUMENTS

| | | | |
|---|---|---|---|
| 2003/0113727 A1* | 6/2003 | Girn | G06Q 50/24 435/6.11 |
| 2008/0076976 A1 | 3/2008 | Sakurai et al. | |
| 2014/0337050 A1 | 11/2014 | Claybrook | |
| 2017/0329924 A1* | 11/2017 | Macpherson | G16H 50/30 |

FOREIGN PATENT DOCUMENTS

| | | |
|---|---|---|
| JP | 2006-059149 A | 3/2006 |
| JP | 2008-077603 A | 4/2008 |
| JP | 2015-92334 A | 5/2015 |
| JP | 2015-132882 A | 7/2015 |
| WO | 96/05306 A2 | 2/1996 |

OTHER PUBLICATIONS

Office Action dated Aug. 16, 2019, issued in counterpart EP application No. 17191589.5. (8 pages).
Extended European Search Report dated Mar. 5, 2018, issued in counterpart European Application No. 17191589.5 (10 pages).
Office Action dated Mar. 3, 2020, issued in counterpart JP Application No. 2016-199281, with English Translation. (10 pages).

* cited by examiner

FAMILY TREE CONSTRUCTION SUPPORTING METHOD AND FAMILY TREE CONSTRUCTION SUPPORTING DEVICE

CROSS-REFERENCE TO RELATED APPLICATION

This application is based upon and claims the benefit of priority of the prior Japanese Patent Application No. 2016-199281 filed on Oct. 7, 2016, the entire contents of which are incorporated herein by reference.

FIELD

A certain aspect of the embodiments is related to a non-transitory computer-readable storage medium, a family tree construction supporting method, and a family tree construction supporting device.

BACKGROUND

There has been known a device that supports the construction of a family tree used in genetic counseling as disclosed in, for example, Japanese Patent Application Publication No. 2015-092334. The nomenclature for constructing a family tree is standardized by the American Society of Human Genetics as disclosed in, for example, R. L. Bennett et al., "Standardized Human Pedigree Nomenclature: Update and Assessment of the Recommendations of the National Society of Genetic Counselors", National Society of Genetic Counselors, Inc., Vol. 17, pp. 424-433, 2008.

SUMMARY

According to an aspect of the embodiments, there is provided a non-transitory computer-readable storage medium storing a family tree construction supporting program causing a computer to execute a process, the process including: receiving a first operation that specifies a person symbol from a plurality of person symbols representing persons present in a family tree; displaying a plurality of first candidate person symbols capable of being connected with the person symbol specified by the received first operation by referring to a first storage unit that stores attribute information with respect to each of a plurality of persons; receiving a second operation that selects a first candidate person symbol from the plurality of first candidate person symbols that have been displayed; and displaying the first candidate person symbol selected by the received second operation while the selected first candidate person symbol is being connected with the person symbol specified by the first operation.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

The aforementioned device supports the construction of a family tree by using individual symbols representing individuals on a family tree and connector symbols representing relationships between the individuals (e.g., a blood relationship, a marital relationship, and the like). However, when the family tree is complicated, the use of the connector symbols may increase, and thus, it may take time and labor to construct the family tree.

Hereinafter, embodiments for carrying out the present case will be described with reference to the accompanying drawings.

Figure 1:
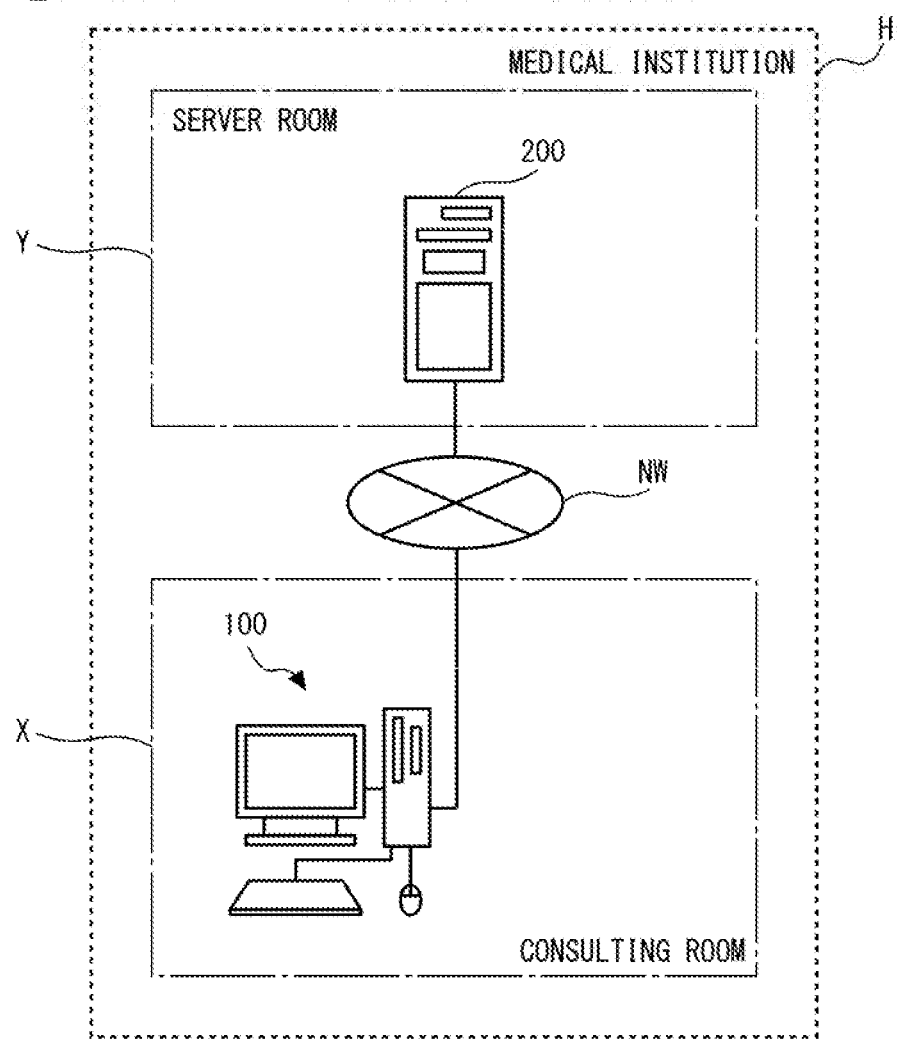
FIG. 1 illustrates an exemplary family tree construction supporting system.

FIG. 1 illustrates an exemplary family tree construction supporting system S. The family tree construction supporting system S is a computer system supporting the construction of a family tree. The family tree construction supporting system S includes a terminal device 100 and a server device 200 as a family tree construction supporting device.

Examples of the terminal device 100 include, but are not limited to, a stationary (desktop) personal computer (PC). The terminal device 100 may be a portable (mobile) PC or a smart device. Examples of the smart device include, but are not limited to, a smartphone and a tablet terminal. FIG. 1 illustrates one terminal device 100, but the number of the terminal devices 100 may be two or more.

The terminal device 100 and the server device 200 are installed in facilities of a medical institution (for example, a hospital) H. More specifically, the terminal device 100 is installed in a consulting room X of the medical institution H.

The server device 200 is installed in a server room Y of the medical institution H. The terminal device 100 and the server device 200 are interconnected through a communication network NW. Examples of the communication network NW include, but are not limited to, a local area network (LAN). The communication network NW may be a wired network or a wireless network. The server device 200 may be installed in a facility such as a data center outside the medical institution H. That is, the server device 200 may be on a cloud. In this case, the Internet is used as the communication network NW, for example.

The terminal device 100 executes various information processing in response to the operation made by a doctor or a counselor (hereinafter, simply referred to as a doctor). For example, when a doctor collects, from a patient, a family member of the patient, or a consulter, information about the family, the terminal device 100 displays various screens and images in response to the operation made by the doctor. For example, when the doctor operates the terminal device 100, the terminal device 100 transmits various information to the server device 200 or receives various information from the server device 200 in response to the operation made by the doctor. The screens displayed on the terminal device 100 will be described later.

The server device 200 executes various information processing relating to the construction of a family tree. More specifically, when receiving the information transmitted from the terminal device 100, the server device 200 executes various information processing based on the received information. For example, when receiving information relating to a request for displaying a screen or an image from the terminal device 100, the server device 200 transmits the screen or image according to the received information to the terminal device 100. Thus, when receiving the screen or image transmitted from the server device 200, the terminal device 100 displays the received screen or image. The details of the server device 200 will be described later.

Figure 2:
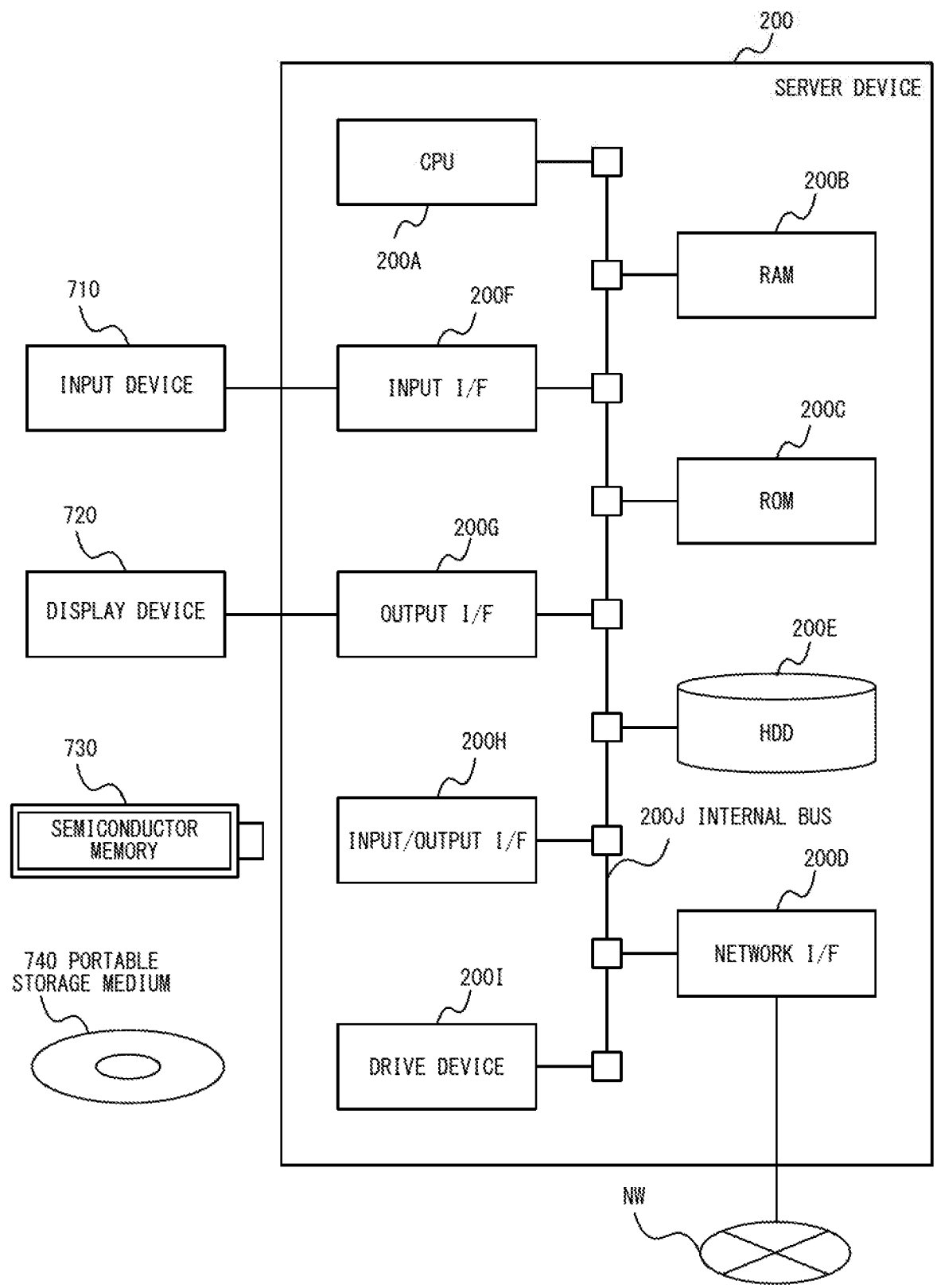
FIG. 2 illustrates a hardware configuration of a server device.

With reference to FIG. 2, a hardware configuration of the server device 200 will be described. The aforementioned terminal device 100 basically has the same hardware configuration as the server device 200, and the description thereof is thus omitted.

FIG. 2 illustrates an exemplary hardware configuration of the server device 200. As illustrated in FIG. 2, the server device 200 includes at least a central processing unit (CPU) 200A, a random access memory (RAM) 200B, a read only memory (ROM) 200C, and a network interface (I/F) 200D. The server device 200 may include at least one of a hard disk drive (HDD) 200E, an input I/F 200F, an output I/F 200G an input/output I/F 200H, and a drive device 200I as necessary. The CPU 200A through the drive device 200I are interconnected by an internal bus 200J. The cooperation of at least the CPU 200A and the RAM 200B achieves a computer.

An input device 710 is coupled to the input I/F 200F. Examples of the input device 710 include, but are not limited to, a keyboard and a mouse. A display device 720 is coupled to the output I/F 200G. Examples of the display device 720 include, but are not limited to, a liquid crystal display. A semiconductor memory 730 is coupled to the input/output I/F 200H. Examples of the semiconductor memory 730 include, but are not limited to, a USB memory and a flash memory. The input/output I/F 200H reads programs and data stored in the semiconductor memory 730. The input I/F 200F and the input/output I/F 200H include, for example, USB ports. The output I/F 200G includes, for example, a display port.

A portable storage medium 740 is inserted into the drive device 200I. Examples of the portable storage medium 740 include, but are not limited to, removal discs such as compact disc (CD)-ROMs and digital versatile discs (DVDs). The drive device 200I reads programs and data stored in the portable storage medium 740. The network I/F 200D includes, for example, a LAN port. The network I/F 200D is coupled to the communication network NW.

The CPU 200A stores programs stored in the ROM 200C or the HDD 200E in the above-described RAM 200B. The CPU 200A stores programs stored in the portable storage medium 740 in the RAM 200B. The execution of the stored programs by the CPU 200A implements various functions described later, and causes various processing described later to be executed. The programs are according to the flowcharts described later.

The functions of the server device 200 will be described with reference to FIG. 3 through FIG. 6.

Figure 3:
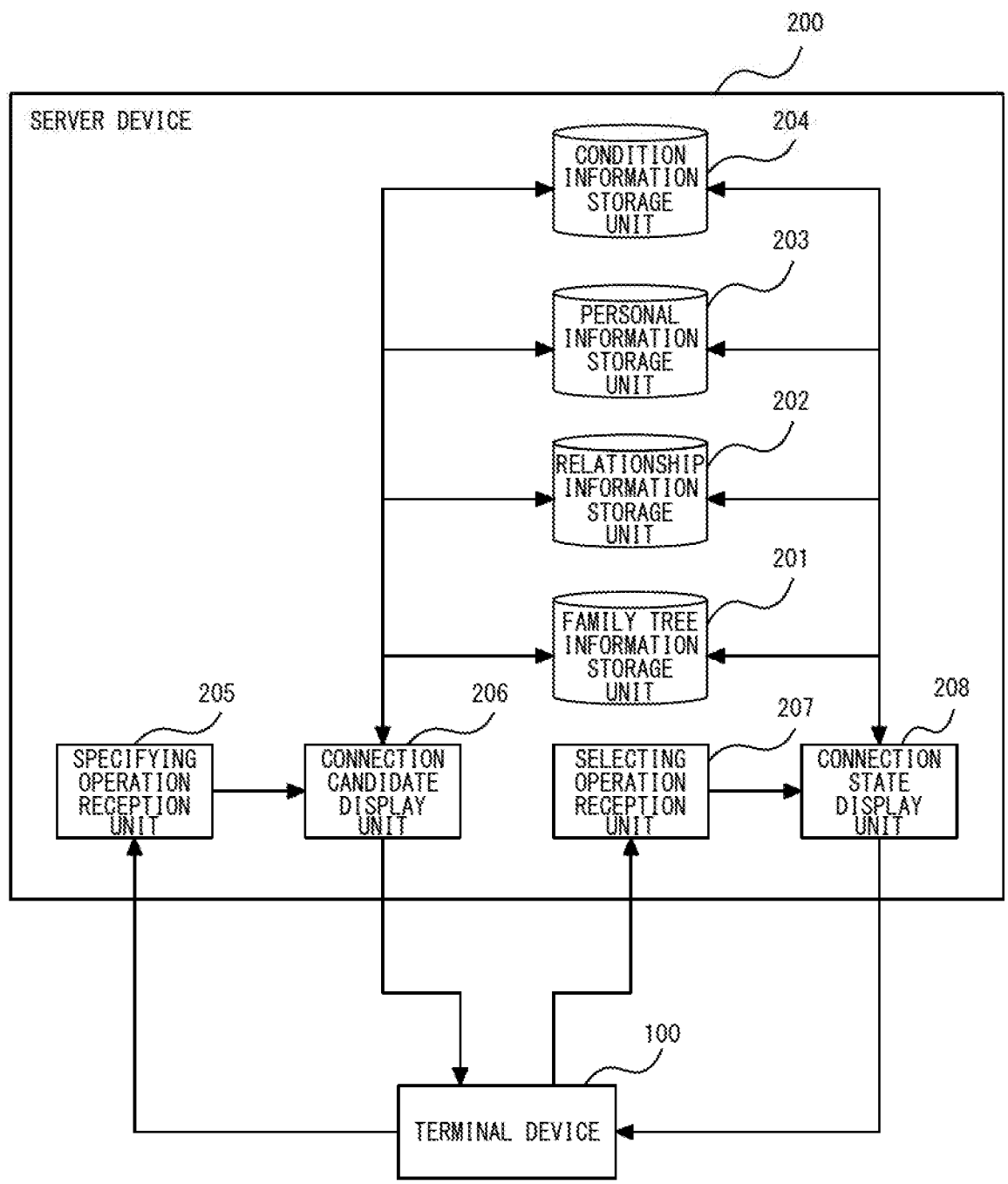
FIG. 3 is an exemplary functional block diagram of the server device.
Figure 4A:
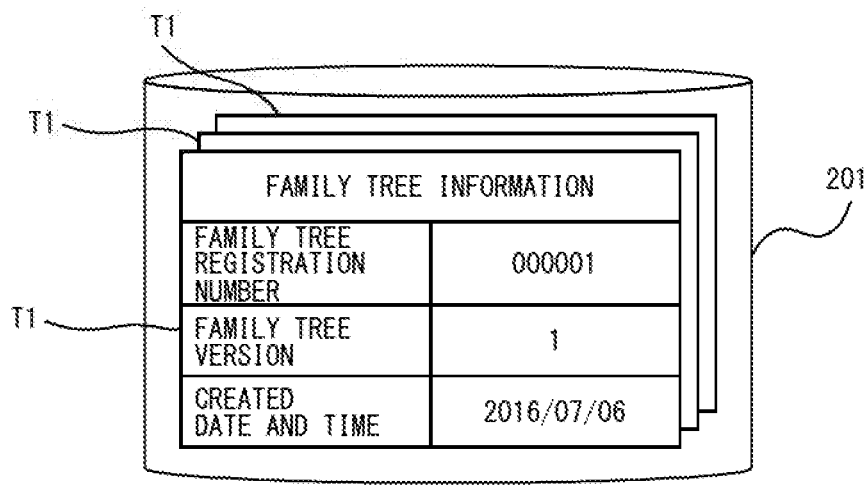
FIG. 4A illustrates a family tree information storage unit.
Figure 4B:
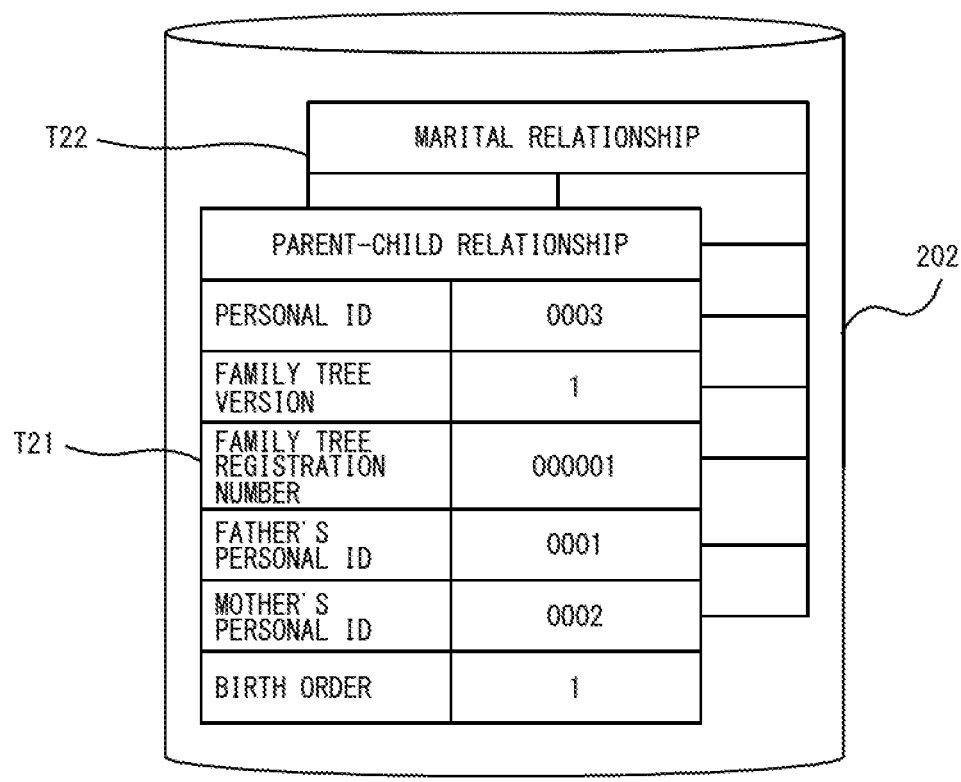
FIG. 4B illustrates a relationship information storage unit.
Figure 5:
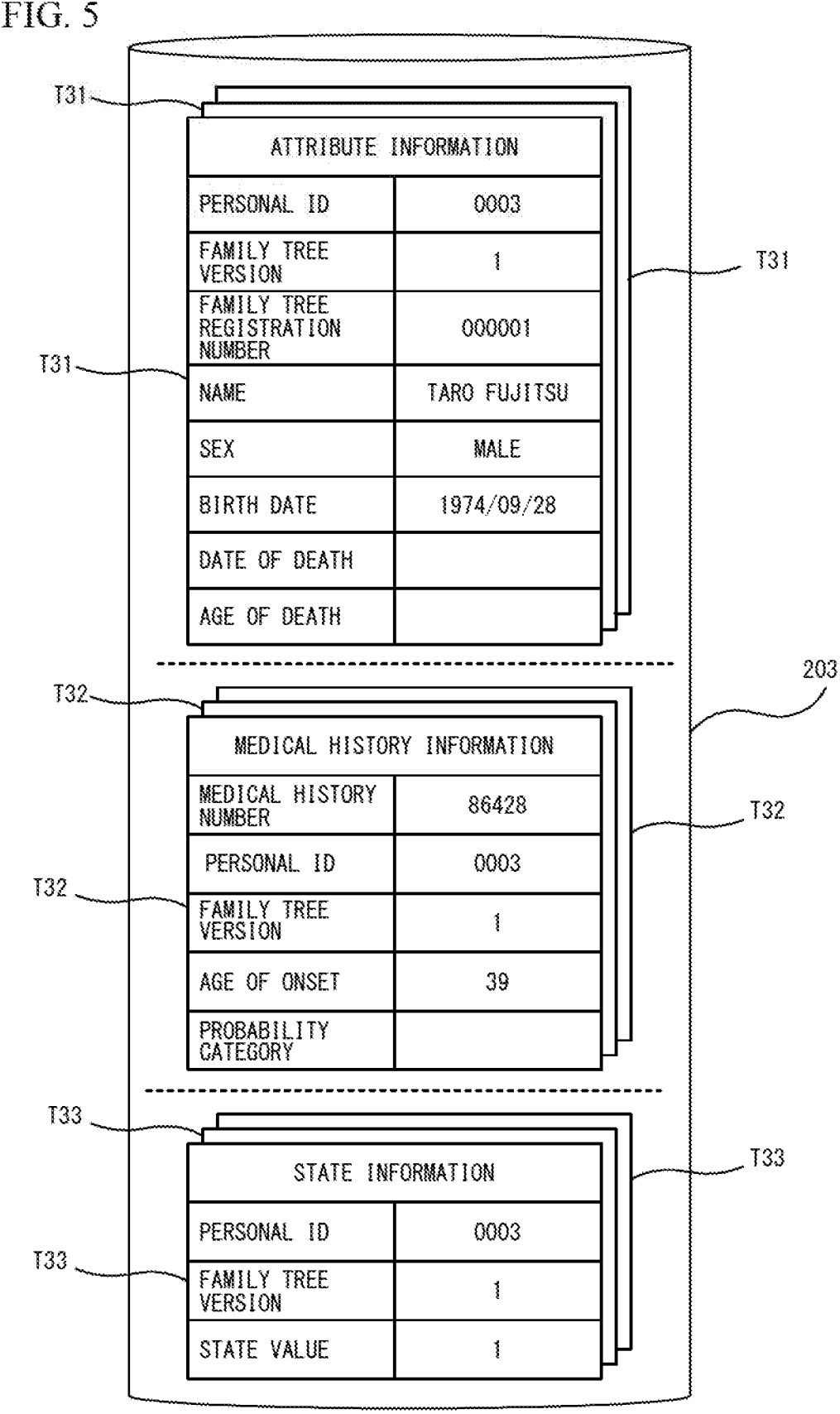
FIG. 5 illustrates a personal information storage unit.
Figure 6:
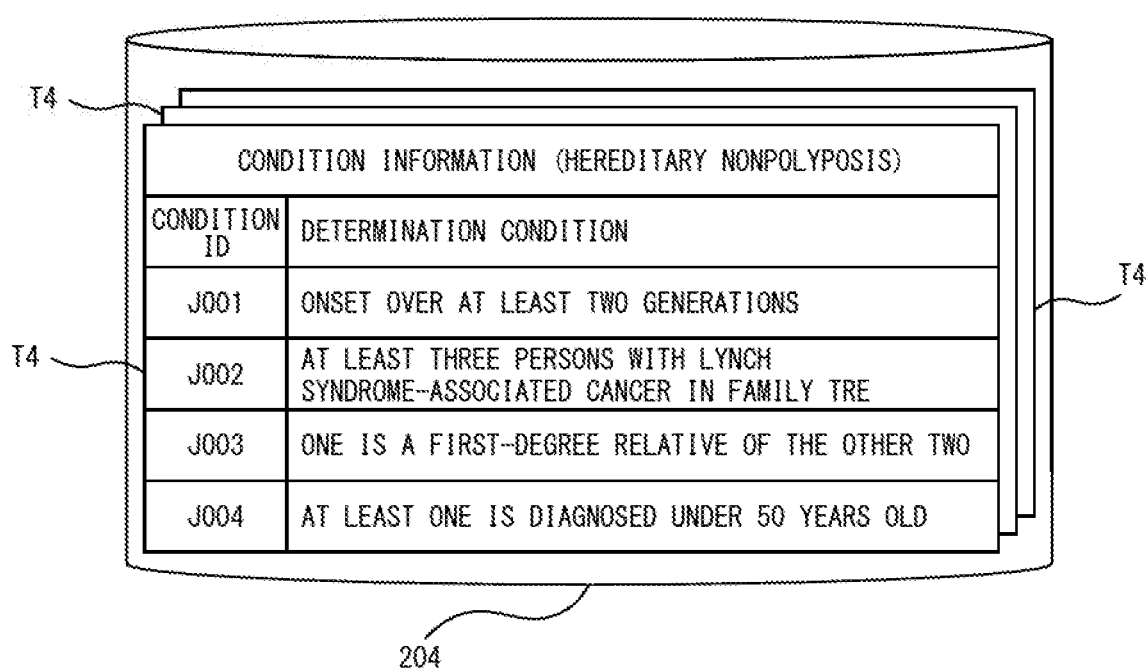
FIG. 6 illustrates a condition information storage unit.

FIG. 3 is an exemplary functional block diagram of the server device 200. FIG. 4A illustrates a family tree information storage unit 201. FIG. 4B illustrates a relationship information storage unit 202. FIG. 5 illustrates a personal information storage unit 203. FIG. 6 illustrates a condition information storage unit 204. As illustrated in FIG. 3, the server device 200 includes the family tree information storage unit 201, the relationship information storage unit 202, the personal information storage unit 203, and the condition information storage unit 204. In addition, the server device 200 includes a specifying operation reception unit 205 as a first reception unit, a connection candidate display unit 206 as a first display unit, a selecting operation reception unit 207 as a second reception unit, and a connection state display unit 208 as a second display unit.

The family tree information storage unit 201, the relationship information storage unit 202, the personal information storage unit 203, and the condition information storage unit 204 may be included in a storage device different from the server device 200. Examples of the storage device include a database server device (hereinafter, referred to as a DB server). In this case, the server device 200 functions as an application server. The terminal device 100 may include the specifying operation reception unit 205, the connection candidate display unit 206, the selecting operation reception unit 207, and the connection state display unit 208. In this case, the server device 200 functions as a DB server.

The family tree information storage unit 201 stores family tree information. The family tree information is information representing a family tree. The family tree information storage unit 201 manages individual family tree information with use of a plurality of family tree information tables T1 as illustrated in FIG. 4A. The family tree information includes a family tree registration number, a family tree version, and a created date and time as constituent elements. The family tree registration number is a number for identifying family tree information. Every time a family tree is newly created, a number discriminable from other family trees is generated and registered. The family tree version is a numerical value representing the version of the family tree information. Every time the family tree is edited and saved, the family tree version is incremented by one. The created date and time is the date and time when the family tree information was created. The family tree information may include other constituent elements such as the name of a person who created the family tree and a deletion flag. For example, when the family tree version is incremented by one, a flag representing the deletion is set to the deletion flag of the previous family tree information. The family tree information is logically deleted by the deletion flag. Thus, the past family tree information remains without being physically deleted.

The relationship information storage unit 202 stores relationship information. The relationship information is information representing a relationship between persons such as a blood relationship and a marital relationship. The relationship information storage unit 202 manages individual relationship information with use of a plurality of relationship information tables T21 and T22 as illustrated in FIG. 4B. More specifically, the relationship information storage unit 202 manages the relationship information with use of the relationship information table T21 representing a parent-child relationship and the relationship information table T22 representing a marital relationship. The relationship information of the parent-child relationship managed by the relationship information table T21 includes a personal ID, the family tree version, the family tree registration number, a father's personal ID, a mother's personal ID, and a birth order as constituent elements. The personal ID, the father's personal ID, and the mother's personal ID are information for identifying a person, the father of the person, and the mother of the person, respectively. The birth order is the birth order of the person. The family tree version and the family tree registration number have been described in the above. On the other hand, the relationship information of the marital relationship managed by the relationship information table T22 includes a spouse's personal ID and a spouse category instead of the father's personal ID, the mother's personal ID, and the birth order described in the above. That is, the relationship information of the marital relationship includes the personal ID, the family tree version, the family tree registration number, the spouse's personal ID, and the spouse category. The spouse's personal ID is information for identifying the spouse of the person. The spouse category is the sex of the spouse of the person. The blood relationship such as the parent-child relationship and the marital relationship representing the relationship with the spouse are identified by the relationship information. Since the relationship information includes the family tree registration number, the relationship information is linked to a family tree.

The personal information storage unit 203 stores personal information. The personal information is divided broadly into attribute information representing the attribute of the person, medical history information representing the medical history of the person, and state information representing the state of the person. Examples of the state of the person include, but are not limited to, a morbidity state, a dead state, and a state that is neither of the morbidity state nor the dead state (for example, a healthy state). The personal information storage unit 203 separately manages the attribute information, the medical history information, and the state information in separate storage regions by respectively using a plurality of attribute information tables T31, a plurality of medical history information tables T32, and a plurality of state information tables T33 as illustrated in FIG. 5.

The attribute information includes the personal ID, the family tree version, the family tree registration number, a name, a sex, a birth date, a date of death, and an age of death as constituent elements. The personal ID, the family tree version, and the family tree registration number have been described in the above. The name, the sex, the birth date, the date of death, and the age of death represent the name, the sex, the birth date, the date of death, and the age of death of the person.

The medical history information includes a medical history number, the personal ID, the family tree version, an age of onset, and a probability category as constituent elements. For example, a date of onset and ICD-10 may be included in addition to the above constituent elements. The medical history number is a number for identifying a disease name. For example, the medical history number "86428" represents the disease name "colorectal cancer". The age of onset represents the age at which symptoms of the disease appeared. The probability category represents categories such as a clinical diagnosis and a definite diagnosis. The personal ID and the family tree version have been described in the above, and the description thereof is thus omitted.

The state information includes the personal ID, the family tree version, and a state value as constituent elements. The state value is a value representing the state of the above person. For example, the state value "1" represents that the state of the person to which the personal ID is assigned is in a morbidity state. The personal ID and the family tree version have been described in the above, and the description thereof is thus omitted. Since all the attribute information, the medical history information, and the state information include the personal ID, they are linked to the relationship information.

The condition information storage unit 204 stores a plurality of sets of condition information with respect to genetic diseases in advance. The condition information is information including the conditions for determining a genetic disease. The condition information storage unit 204 manages a plurality of sets of condition information with respect to genetic diseases by using a plurality of condition information tables T4 as illustrated in FIG. 6. FIG. 6 presents the condition information of hereditary nonpolyposis, which is one of genetic diseases, as an example. The condition information includes a plurality of condition records including a condition ID and a determination condition as constituent elements. The condition ID is identification information for identifying the determination condition. The determination condition represents the condition for determining the genetic disease. Although details will be described later, when the aforementioned medical history information satisfies one of the determination conditions of the condition records of a specific genetic disease, the determination condition of the condition record that has not been satisfied is displayed on the terminal device 100. The condition information storage unit 204 may store information about a past record of onset of the disease in a family structure similar to the family structure present in the family tree. When the probability of the person developing a disease is equal to or greater than a predetermined value based on the past record information, information about an examination to be recommended is displayed on the terminal device 100.

The specifying operation reception unit 205 receives various requests transmitted from the terminal device 100. For example, the specifying operation reception unit 205 receives a specifying operation that specifies one person symbol from person symbols representing persons present in the family tree. The specifying operation is transmitted from the terminal device 100. The specifying operation includes information about the specified person symbol (for example, information about the position in the screen and the attribute information). When receiving the specifying operation, the specifying operation reception unit 205 transmits the received specifying operation to the connection candidate display unit 206. The person symbol may be referred to as an icon. The icon is an image having a specific size that expresses the use or function of a program or contents of a file by a diagram, a picture, or a symbol.

The connection candidate display unit 206 refers to the personal information storage unit 203, and displays candidate person symbols capable of being connected with the person symbol specified by the specifying operation received by the specifying operation reception unit 205 on the terminal device 100. More specifically, the connection candidate display unit 206 transmits information that causes the terminal device 100 to display the candidate person symbols to the terminal device 100. This process causes the terminal device 100 to display the candidate person symbols capable of being connected with the person symbol specified by the specifying operation. When displaying the candidate person symbols, the connection candidate display unit 206 displays the candidate person symbols representing parents, the candidate person symbol representing a sibling, and the candidate person symbol representing a child in different manners. Furthermore, the connection candidate display unit 206 displays candidate person symbols for identifying the state of the person represented by the person symbol specified by the specifying operation together with the candidate person symbols on the terminal device 100. More specifically, the connection candidate display unit 206 transmits information that causes the terminal device 100 to display the candidate person symbols for identifying the state of the person together with the candidate person symbols to the terminal device 100. This process causes the terminal device 100 to display the candidate person symbols for identifying the state of the person represented by the person symbol specified by the specifying operation together with the candidate person symbols.

The selecting operation reception unit 207 receives a selecting operation that selects a candidate person symbol from the candidate person symbols displayed by the connection candidate display unit 206. The selecting operation reception unit 207 also receives another selecting operation that selects another candidate person symbol from the candidate person symbols for identifying the state of the person displayed by the connection candidate display unit 206. These selecting operations are transmitted from the terminal device 100. The selecting operation includes information about the selected candidate person symbol or the selected candidate person symbol for identifying the state of the person. When receiving a selecting operation, the selecting operation reception unit 207 transmits the received selecting operation to the connection state display unit 208.

The connection state display unit 208 displays the candidate person symbol selected by the selecting operation received by the selecting operation reception unit 207 on the terminal device 100 while the selected candidate person symbol is being connected with the person symbol specified by the specifying operation. More specifically, the connection state display unit 208 transmits information that causes the candidate person symbol selected by the selecting operation to be displayed while the selected candidate person symbol is being connected with the person symbol specified by the specifying operation to the terminal device 100. This process causes the terminal device 100 to display the candidate person symbol selected by the selecting operation while the selected candidate person symbol is being connected with the person symbol specified by the specifying operation. The connection state display unit 208 changes the person symbol specified by the specifying operation to the candidate person symbol, selected by the selecting operation received by the selecting operation reception unit 207, for identifying the state of the person. More specifically, the connection state display unit 208 transmits information that changes the person symbol specified by the specifying operation to the candidate person symbol, selected by the selecting operation to the terminal device 100, for identifying the state of the person. This process causes the terminal device 100 to change the person symbol specified by the specifying operation to the candidate person symbol, selected by the selecting operation, for identifying the state of the person.

A description will next be given of operations of the server device 200.

Figure 7:
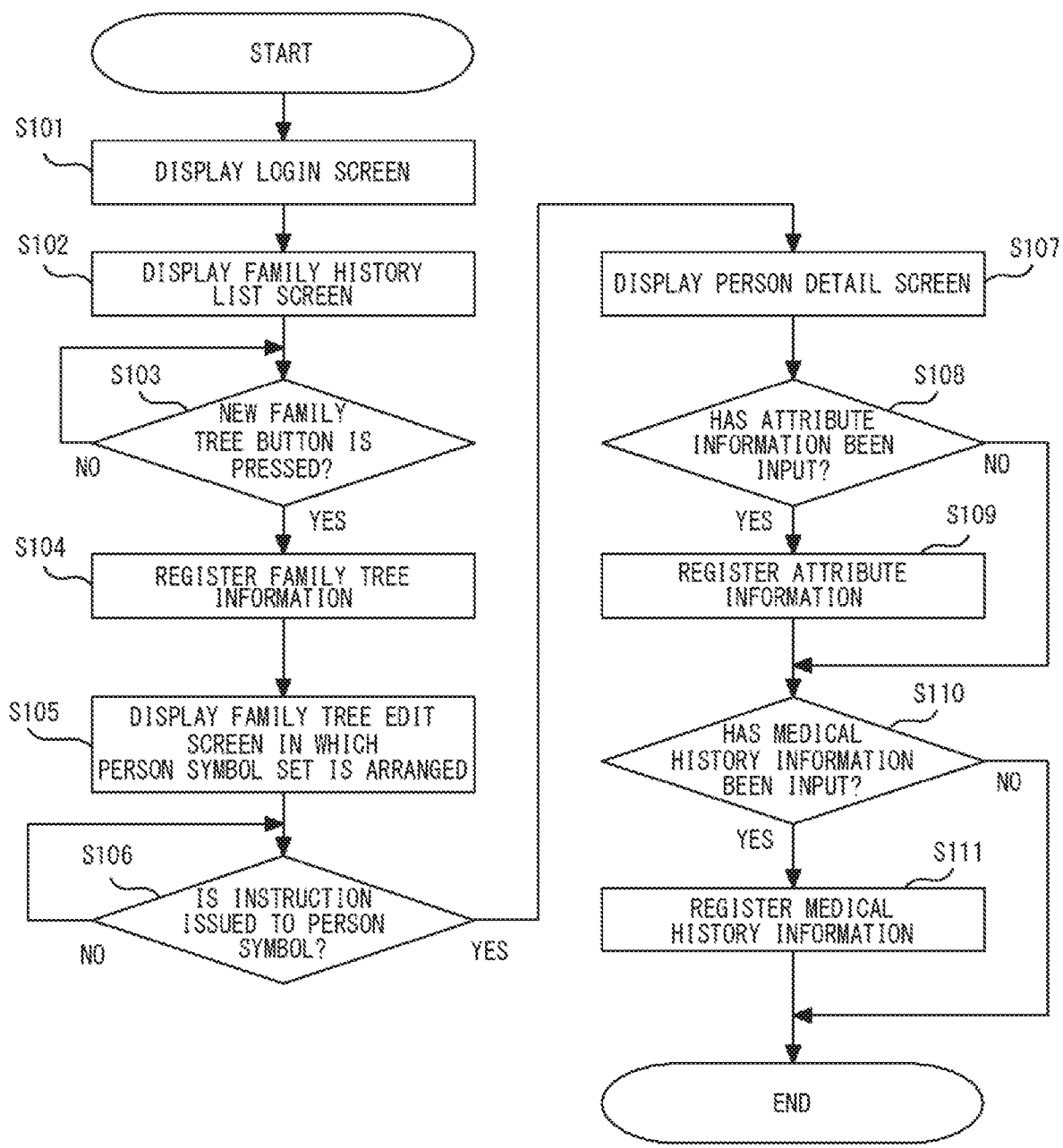
FIG. 7 is a flowchart of an exemplary operation of the server device.
Figure 8A:
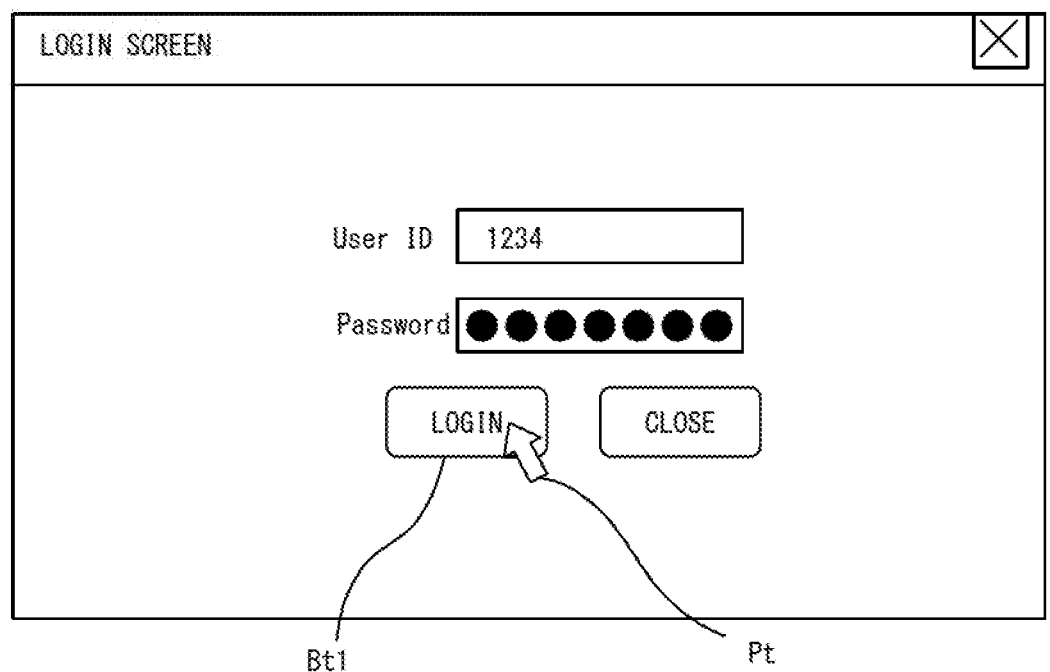
FIG. 8A illustrates a login screen.
Figure 8B:
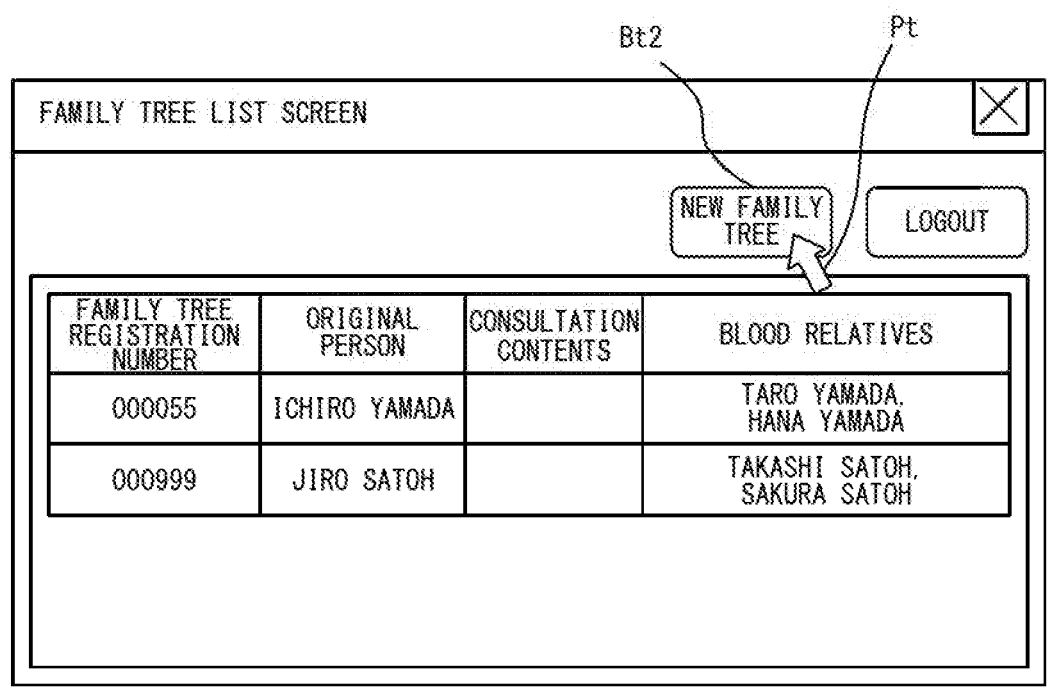
FIG. 8B illustrates a family history list screen.
Figure 9A:
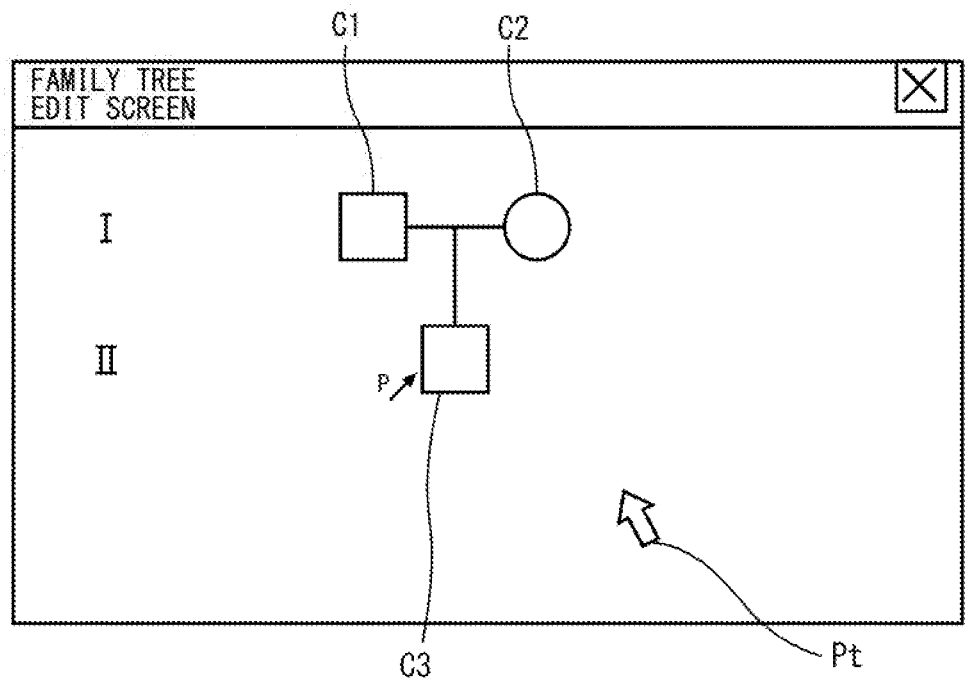
FIG. 9A illustrates an example of a family tree edit screen.
Figure 9B:
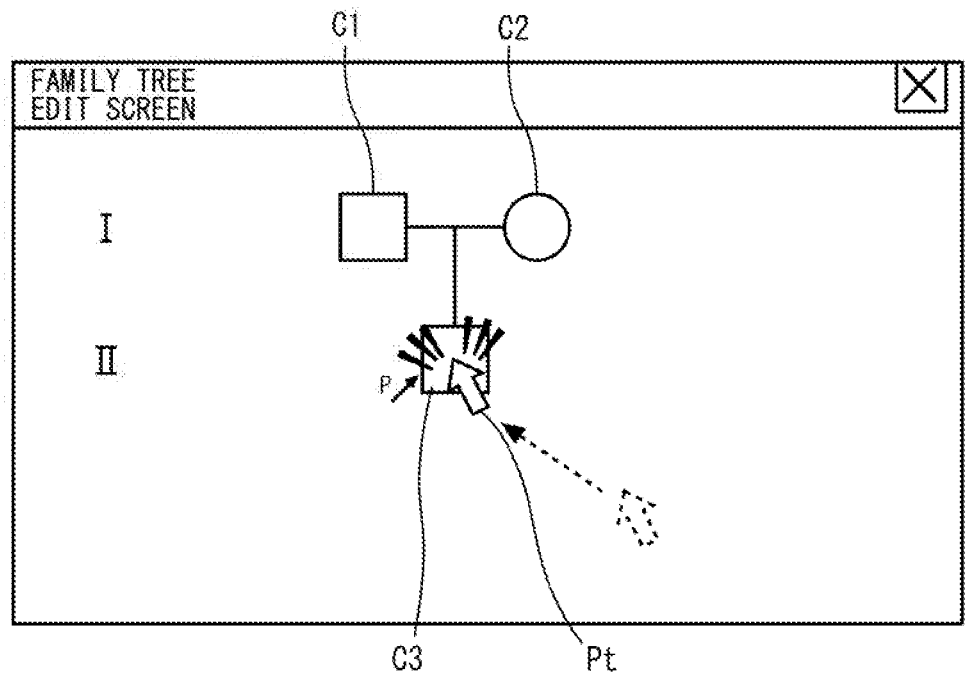
FIG. 9B illustrates another example of the family tree edit screen.
Figure 10A:
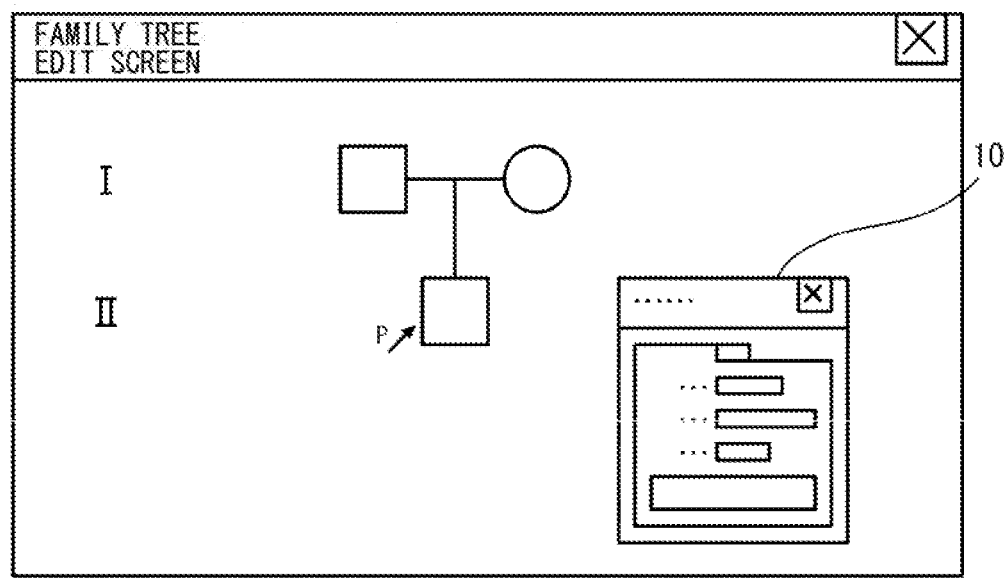
FIG. 10A and FIG. 10B illustrate other examples of the family tree edit screen.
Figure 10B:
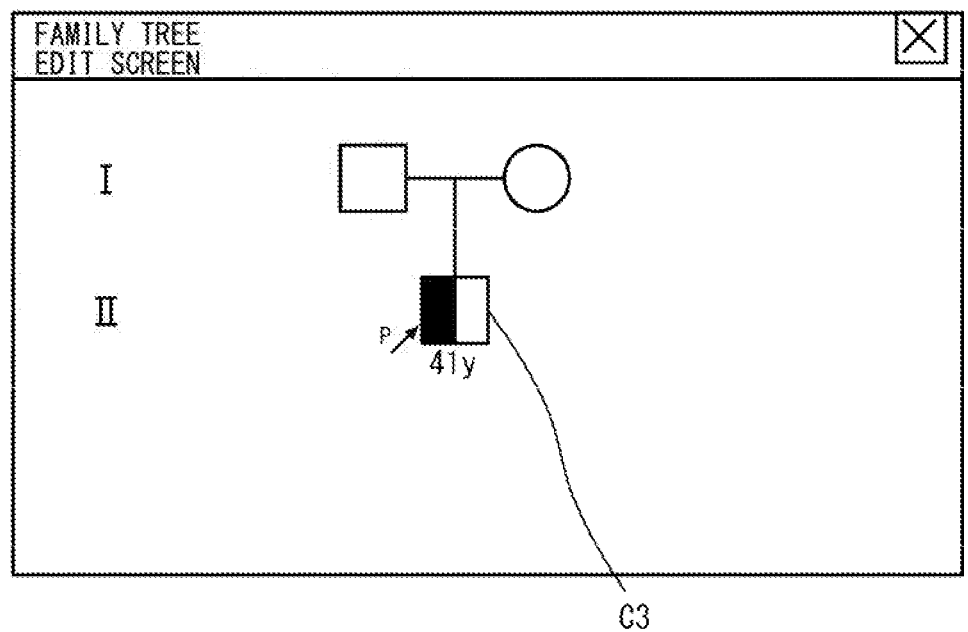
Figure 11:
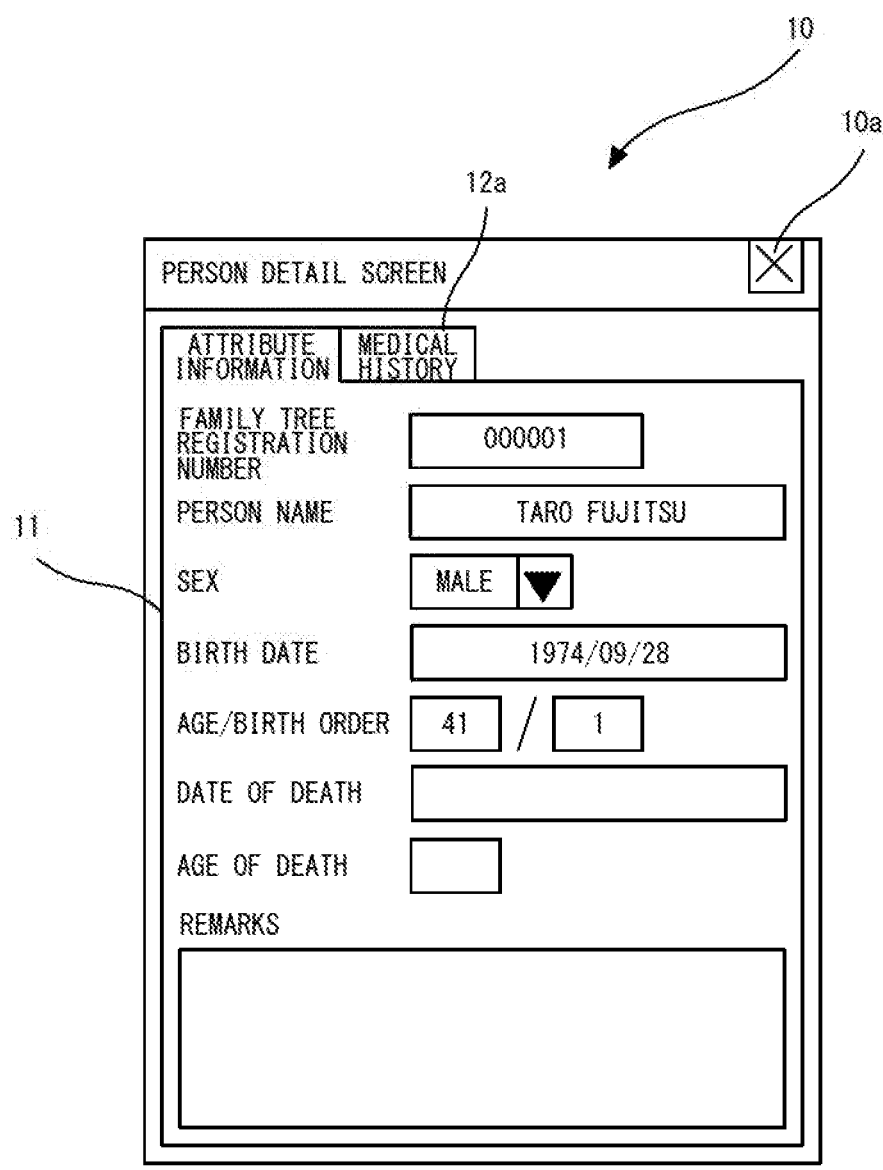
FIG. 11 illustrates an example of a person detail screen.
Figure 12:
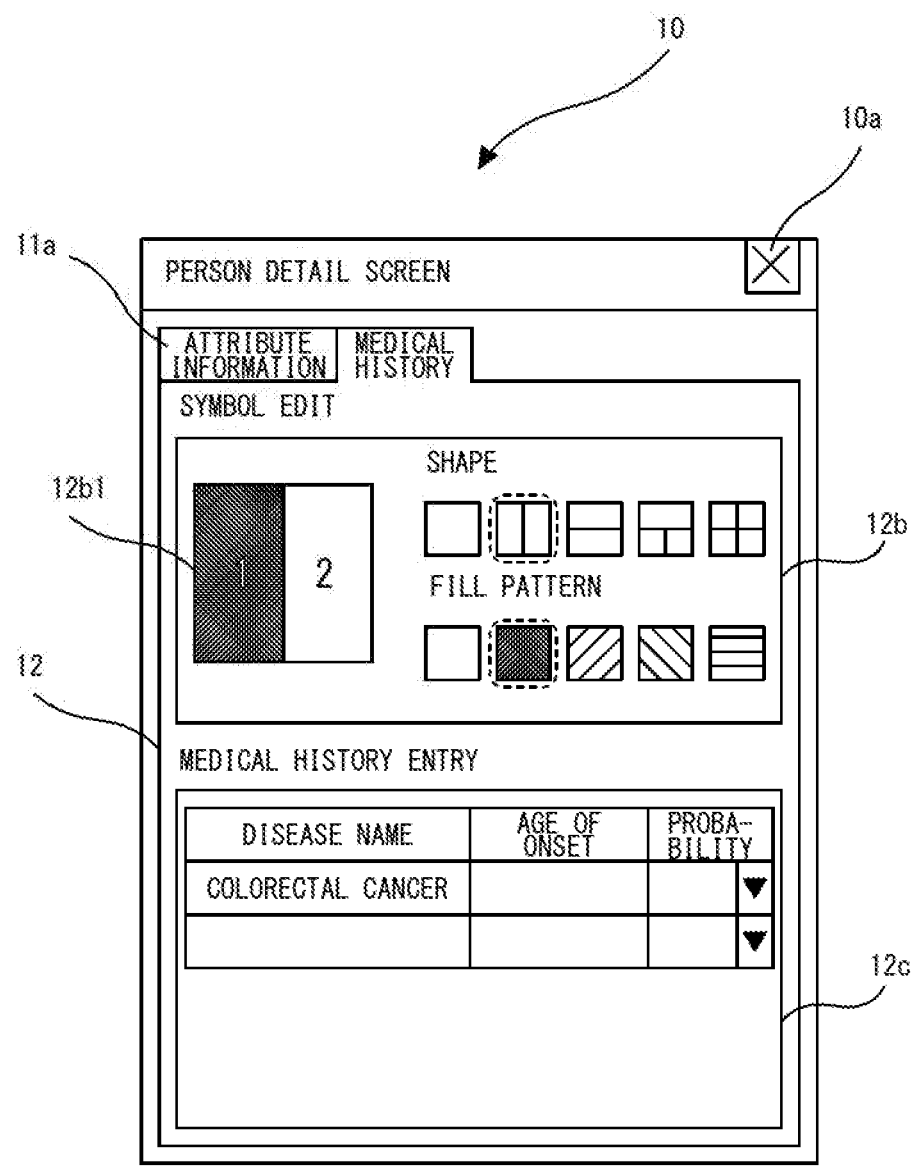
FIG. 12 illustrates another example of the person detail screen.

FIG. 7 is a flowchart of an exemplary operation of the server device 200. FIG. 8A illustrates a login screen. FIG. 8B illustrates a family history list screen. FIG. 9A illustrates a family tree edit screen. FIG. 9B, FIG. 10A, and FIG. 10B illustrate other examples of the family tree edit screen. FIG. 11 illustrates a person detail screen. FIG. 12 illustrates another example of the person detail screen.

As illustrated in FIG. 7, the connection candidate display unit 206 displays a login screen (step S101). More specifically, when the specifying operation reception unit 205 receives a request for the transmission of a function supporting the construction of a family tree from the terminal device 100, the connection candidate display unit 206 transmits information that causes the terminal device 100 to display the login screen to the terminal device 100. This process causes the terminal device 100 to display the login screen as illustrated in FIG. 8A.

Upon completion of the processing of the step S101, the connection candidate display unit 206 displays a family history list screen (step S102). More specifically, as illustrated in FIG. 8A, when a user ID and a password are input in the login screen and an image representing a button for login (hereinafter, an image representing a button will be simply referred to as a button) Bt1 is pressed with a pointer Pt, the terminal device 100 transmits the input user ID and the input password as credentials to the server device 200. When receiving the credentials, the specifying operation reception unit 205 of the server device 200 checks the received credentials against the credentials preliminarily registered in the server device 200. When the result of the checking by the specifying operation reception unit 205 is positive, the connection candidate display unit 206 extracts the family tree information from the family tree information storage unit 201. Then, the connection candidate display unit 206 extracts the relationship information and the personal information according to the extracted family tree information respectively from the relationship information storage unit 202 and the personal information storage unit 203, and transmits information that causes the terminal device 100 to display the family history list screen to the terminal device 100. This process causes the terminal device 100 to display the family history list screen including the family tree information, the relationship information, and the personal information as illustrated in FIG. 8B. The family tree information already registered is displayed on the family history list screen illustrated in FIG. 8B.

Upon completion of the processing of the step S102, the connection candidate display unit 206 waits until a new family tree button is pressed (step S103: NO). When the new family tree button is pressed (step S103: YES), the connection candidate display unit 206 registers family tree information (step S104). More specifically, when a button Bt2 representing the new family tree registration is pressed by the pointer Pt on the family history list screen as illustrated in FIG. 8B, the terminal device 100 transmits information that requests the registration of a new family tree to the server device 200. When the specifying operation reception unit 205 of the server device 200 receives the information that requests the registration of a new family tree, the connection candidate display unit 206 generates a family tree registration number, and registers new family tree information (see FIG. 4A) in the family tree information storage unit 201.

Upon completion of the processing of the step S104, the connection candidate display unit 206 displays the family tree edit screen in which a person symbol set is arranged (step S105). More specifically, the connection candidate display unit 206 transmits information that causes the terminal device 100 to display the family tree edit screen in which the person symbol set is arranged to the terminal device 100. This process causes the terminal device 100 to display the family tree edit screen in which the person symbol set is arranged as illustrated in FIG. 9A. The person symbol set includes a person symbol C3 representing an original person, a person symbol C1 representing the father of the original person, and a person symbol C2 representing the mother of the original person. The original person is a person who triggered finding of the family tree having genetic illness. This person symbol set represents that the original person was born from the father and the mother. The square person symbols C1 and C3 represent males, and the circular person symbol C2 represents a female. The original person is identified by an arrow with a character P attached. Instead of the above notation, a person symbol identified by an arrow without the character P attached (not illustrated) represents a consulter, but the detailed nomenclature is basically standardized by the American Society of Human Genetics.

Generation numbers align at the left side of the person symbol set so as to correspond to respective generations. More specifically, the generation number "I", which indicates that the person symbols C1 and C2 are the first generations in the person symbol set, is arranged at the left side of the person symbols C1 and C2. The generation number "II", which indicates that the person symbol C3 is the second generation in the person symbol set, is arranged at the left side of the person symbol C3. This configuration allows the doctor to easily understand the generations of the person symbols C1 through C3.

Upon completion of the processing of the step S105, the connection candidate display unit 206 waits until an instruction is issued to one of the person symbols (step S106: NO). When an instruction is issued to one of the person symbols (step S106: YES), the connection candidate display unit 206 displays a person detail screen (step S107). For example, as illustrated in FIG. 9B, when an instruction is issued to the person symbol C3 by the pointer Pt on the family history list screen, the terminal device 100 transmits information that requests the person detail screen to the server device 200. The instruction to the person symbol C3 is, for example, a specific operation such as a double click. When the specifying operation reception unit 205 of the server device 200 receives the information that requests the person detail screen, the connection candidate display unit 206 transmits information that causes the terminal device 100 to display the person detail screen to the terminal device 100. This process causes the terminal device 100 to display a person detail screen 10 as illustrated in FIG. 10A. The displayed position of the person detail screen 10 may be a position at which at least a part of the person detail screen 10 overlaps with the family tree edit screen or a position at which the person detail screen 10 does not overlap with the family tree edit screen.

The person detail screen 10 includes an attribute input screen 11 for inputting the attribute information as illustrated in FIG. 11, and a medical history input screen 12 for inputting the medical history information as illustrated in FIG. 12. For example, when a tab 12a, which is a part of the medical history input screen 12, is specified (for example, clicked) while the attribute input screen 11 is being displayed anteriorly to the medical history input screen 12 as illustrated in FIG. 11, the terminal device 100 displays the medical history input screen 12 anteriorly to the attribute input screen 11 as illustrated in FIG. 12. In contrast, when a tab 11a, which is a part of the attribute input screen 11, is specified while the medical history input screen 12 is being displayed anteriorly to the attribute input screen 11 as illustrated in FIG. 12, the terminal device 100 displays the attribute input screen 11 anteriorly to the medical history input screen 12 as illustrated in FIG. 11.

The attribute input screen 11 includes a plurality of entry fields for inputting the attributes of the person and a remarks column as illustrated in FIG. 11. The doctor gathers from a patient, the family member of the patient, or a consulter the attributes of the patient and the family member, and then inputs the gathered attributes to respective entry fields and inputs the contents other than the attributes to the remarks column. On the other hand, the medical history input screen 12 includes a symbol editing part 12b for changing a display mode of the person symbol to which an instruction is issued, and a medical history entry part 12c for inputting the medical history of the person as illustrated in FIG. 12. The doctor gathers from a patient, the family member of the patient, or a consulter the medical histories of the patient and the family member, and then selects a shape and a fill pattern in the symbol editing part 12b according to the gathered medical history. When the shape and the fill pattern are selected, the terminal device 100 changes the display mode of a person symbol 12b1. For example, when the doctor selects a shape that divides the person symbol 12b1 into four, the doctor becomes able to select four fill patterns. Additionally, the doctor inputs the gathered medical history in each entry field of the medical history entry part 12c. Especially when a plurality of medical histories are input, the doctor selects the shape and the fill pattern indicating that a plurality of medical histories have been input. This causes the terminal device 100 to change the display mode of the person symbol 12b1 in a manner that makes it recognizable that the plurality of medical histories have been input. When an instruction is issued to the person symbol C2 representing a female, the person symbol 12b1 is displayed in a circular shape.

Upon completion of the processing of the step S107, the connection candidate display unit 206 determines whether the attribute information has been input (step S108). For example, as illustrated in FIG. 11, when the attributes are input to respective entry fields, and a close button 10a or the tab 12a on the person detail screen 10 is specified, the connection candidate display unit 206 determines that the attribute information has been input (step S108: YES), and registers the input attributes in the personal information storage unit 203 as the attribute information (step S109). At this time, the connection candidate display unit 206 also registers the state information by using the attribute information. For example, when the date of death is included in the attribute information, the connection candidate display unit 206 registers the state information including the state value representing the dead state. On the other hand, when the attribute is not input to any entry field, and the close button 10a or the tab 12a on the person detail screen 10 is specified, the connection candidate display unit 206 determines that the attribute information was not input (step S108: NO), and skips the process of the step S109.

When the process of the step S109 is completed or skipped, the connection candidate display unit 206 determines whether the medical history information has been input (step S110). For example, as illustrated in FIG. 12, when the shape and the fill pattern in the symbol editing part 12b are selected, the medical history is input to each entry field of the medical history entry part 12c, and the close button 10a or the tab 11a on the person detail screen 10 is specified, the connection candidate display unit 206 determines that the medical history information has been input (step S110: YES), and registers the number for identifying the input medical history and the like in the personal information storage unit 203 as the medical history information (step S111).

On the other hand, when the shape and the fill pattern in the symbol editing part 12b are not selected, the medical history is not input to any entry field of the medical history entry part 12c, and the close button 10a or the tab 11a in the person detail screen 10 is specified, the connection candidate display unit 206 determines that the medical history information was not input (step S110: NO), and skips the process of the step S111. When the process of the step S111 is completed or skipped, the connection candidate display unit 206 ends the process.

As described above, when the attribute information and the medical history information are input, the connection candidate display unit 206 changes the display mode of the person symbol C3 to which an instruction has been issued based on the contents of the input attribute information and the input medical history information as illustrated in FIG. 10B, and displays the contents (for example, the age) of the attribute information under the person symbol C3. When the same instruction as the instruction to the person symbol C3 is issued to the person symbols C1 and C2, the attribute information and the medical history information are registered for the person symbols C1 and C2 in addition to those for the person symbol C3, and reflected on the family tree edit screen.

A description will next be given of a process of connecting the person symbols and a process of changing the display mode of the person symbol with reference to FIG. 13 through FIG. 17B.

Figure 13:
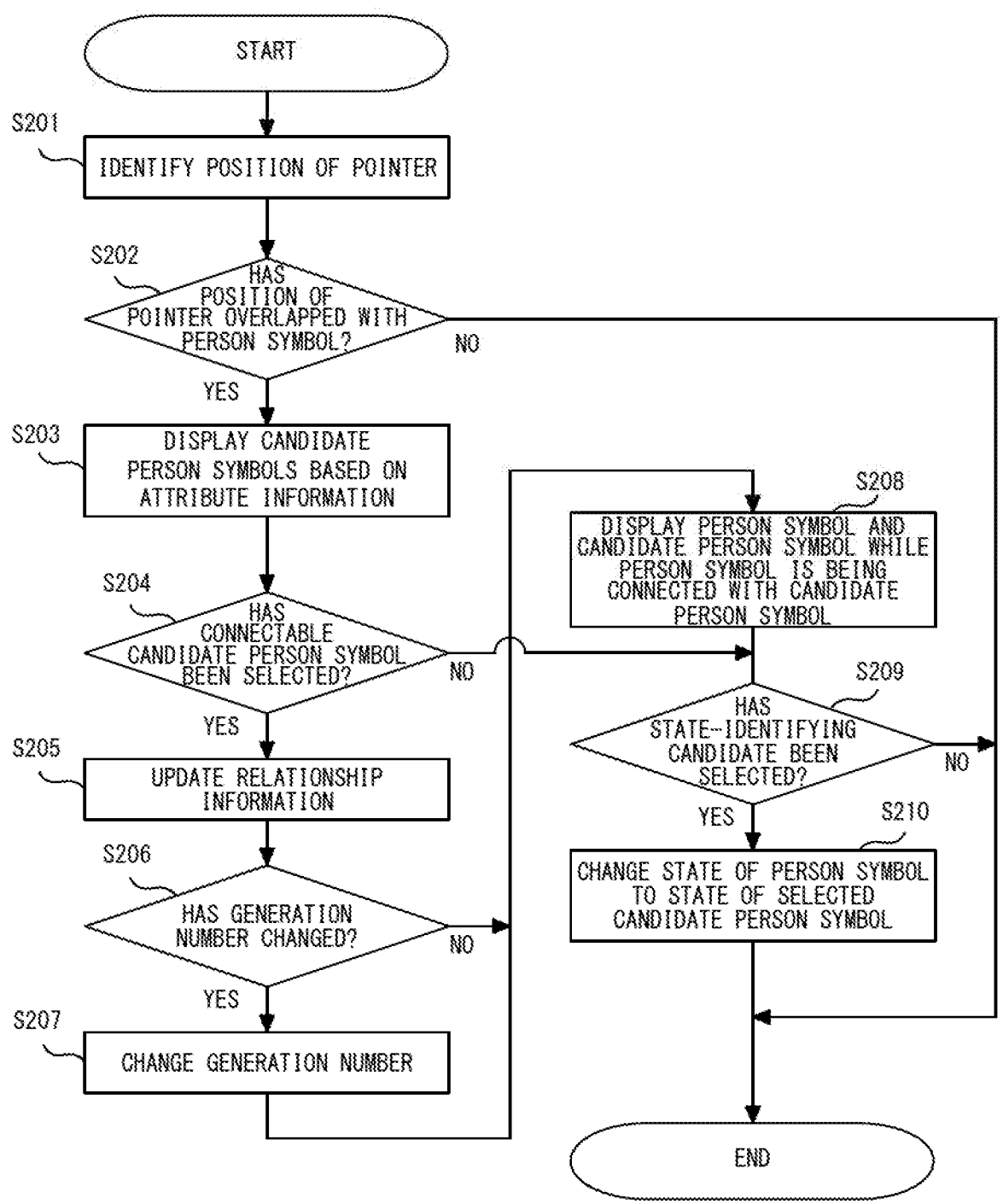
FIG. 13 is a flowchart of another exemplary operation of the server device.

FIG. 13 is a flowchart of another exemplary operation of the server device 200. FIG. 14A through FIG. 17B illustrate other examples of the family tree edit screen. As illustrated in FIG. 13, the connection candidate display unit 206 identifies the position of the pointer (step S201). More specifically, when the pointer Pt moves on the family tree edit screen, the terminal device 100 transmits the moving amount of and the moving direction of the pointer Pt to the server device 200 as move information. When the specifying operation reception unit 205 of the server device 200 receives the move information transmitted from the terminal device 100, the connection candidate display unit 206 identifies the position of the pointer Pt in the family tree edit screen based on the move information received by the specifying operation reception unit 205.

Upon completion of the processing of the step S201, the connection candidate display unit 206 determines whether the position of the pointer has overlapped with the person symbol (step S202). When determining that the position of the pointer has not overlapped with the person symbol (step S202: NO), the connection candidate display unit 206 skips the subsequent processes, and ends the process.

Figure 14A:
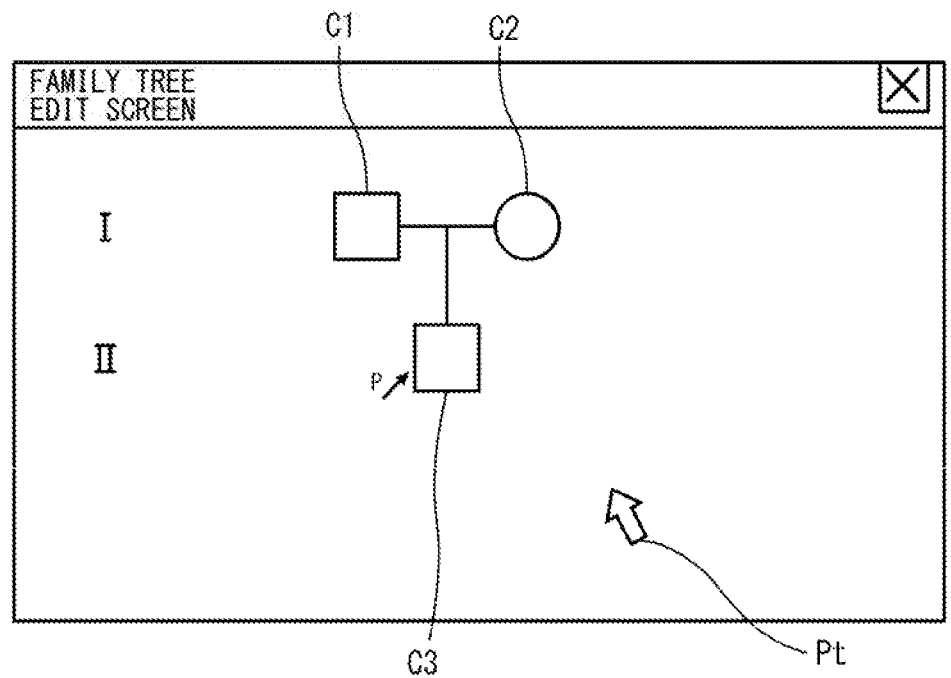
FIG. 14A and FIG. 14B illustrate other examples of the family tree edit screen.
Figure 14B:
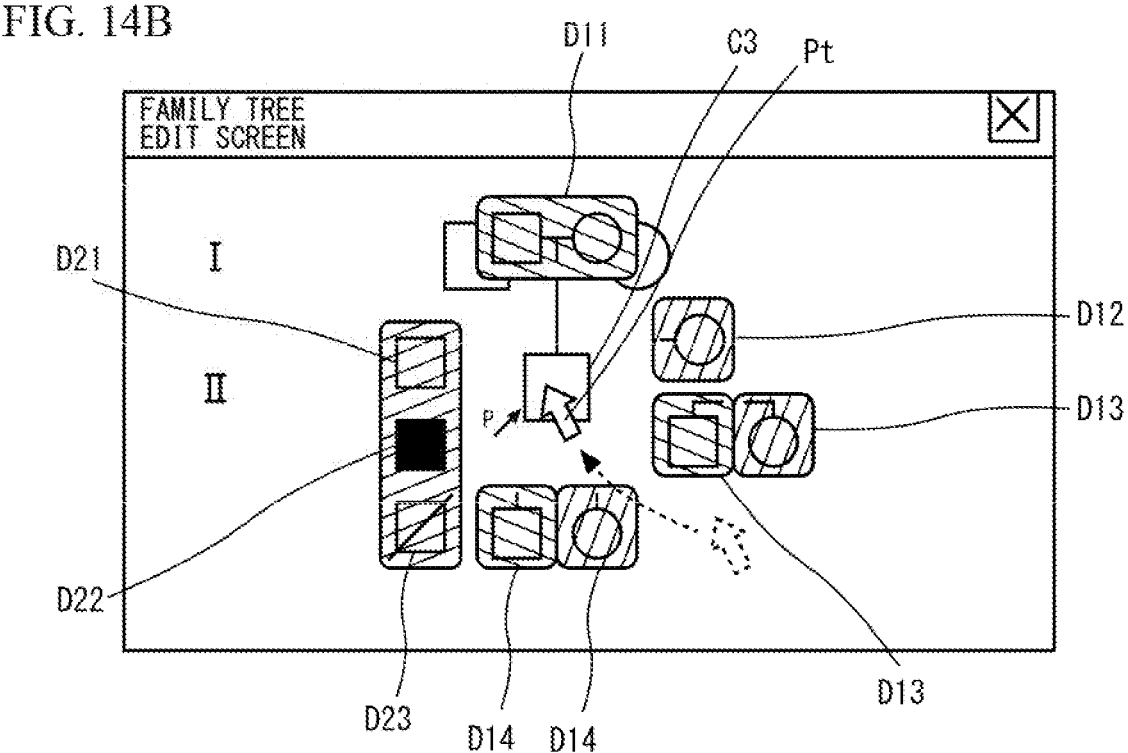

On the other hand, when determining that the position of the pointer has overlapped with the person symbol (step S202: YES), the connection candidate display unit 206 displays candidate person symbols based on the attribute information (step S203). For example, when the state is changed from the state where the position of the pointer Pt overlaps with none of the person symbols C1 through C3 as illustrated in FIG. 14A to the state where the position of the pointer Pt overlaps with the person symbol C3 as illustrated in FIG. 14B (so-called mouse-on state), the connection candidate display unit 206 determines that the position of the pointer Pt has overlapped with the person symbol C3. When determining that the position of the pointer Pt has overlapped with the person symbol C3, the connection candidate display unit 206 causes the terminal device 100 to display candidate person symbols D11, D12, D13, and D14 capable of being connected with the person symbol C3 and candidate person symbols D21, D22, and D23 for identifying the state of the person symbol C3 based on the attribute information of the person symbol C3 so that the candidate person symbols surround the person symbol C3. More specifically, the connection candidate display unit 206 transmits information that causes the terminal device 100 to display the candidate person symbols D11, D12, D13, D14, D21, D22, and D23 to the terminal device 100. This process causes the terminal device 100 to display the candidate person symbols D11, D12, D13, D14, D21, D22, and D23 so that the candidate person symbols surround the person symbol C3 as illustrated in FIG. 14B.

Especially, since the person symbol C3 represents a male, the terminal device 100 displays the candidate person symbol D12 representing a female based on the attribute information. Thus, if the person symbol C3 has a circular shape representing a female, the terminal device 100 displays a candidate person symbol with a square shape representing a male (not illustrated) based on the attribute information. When the specifying operation reception unit 205 receives an operation (e.g., a click) specifying the person symbol C3 after the position of the pointer Pt has overlapped with the person symbol C3, the connection candidate display unit 206 may display the candidate person symbols D11, D12, D13, D14, D21, D22, and D23 for the person symbol C3.

Figure 15A:
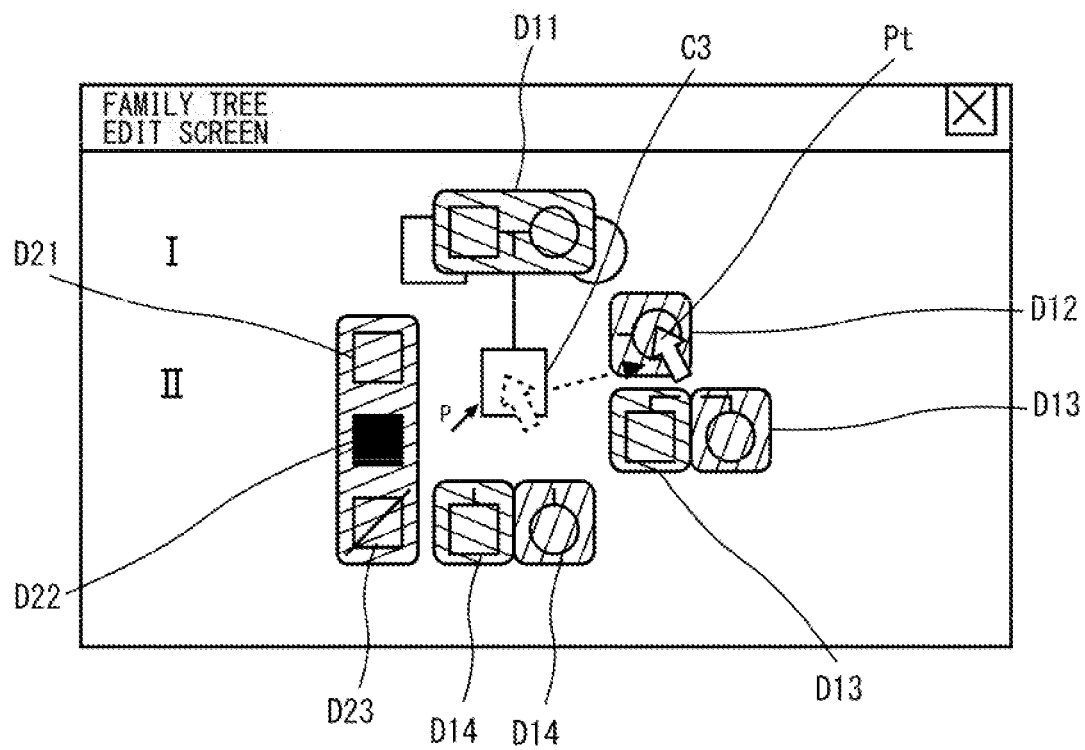
FIG. 15A and FIG. 15B illustrate other examples of the family tree edit screen.

Upon completion of the processing of the step S203, the connection state display unit 208 determines whether a connectable candidate person symbol has been selected (step S204). When determining that a connectable candidate has been selected (step S204: YES), the connection state display unit 208 updates the relationship information (step S205). For example, when the selecting operation that selects the candidate person symbol D12 from the candidate person symbols D11, D12, D13, and D14 capable of being connected with the person symbol C3 has been conducted as illustrated in FIG. 15A, the terminal device 100 transmits the selecting operation including the selected candidate person symbol D12 to the server device 200. When the selecting operation reception unit 207 of the server device 200 receives the selecting operation from the terminal device 100, the connection state display unit 208 accesses the relationship information storage unit 202 and updates the relationship information of the marital relationship.

Upon completion of the processing of the step S205, the connection state display unit 208 determines whether the generation number has changed (step S206). When determining that the generation number has changed (step S206: YES), the connection state display unit 208 changes the generation number (step S207). On the other hand, when determining that the generation number has not changed (step S206: NO), the connection state display unit 208 skips the process of the step S207. Details of changing the generation number will be described later.

Figure 15B:
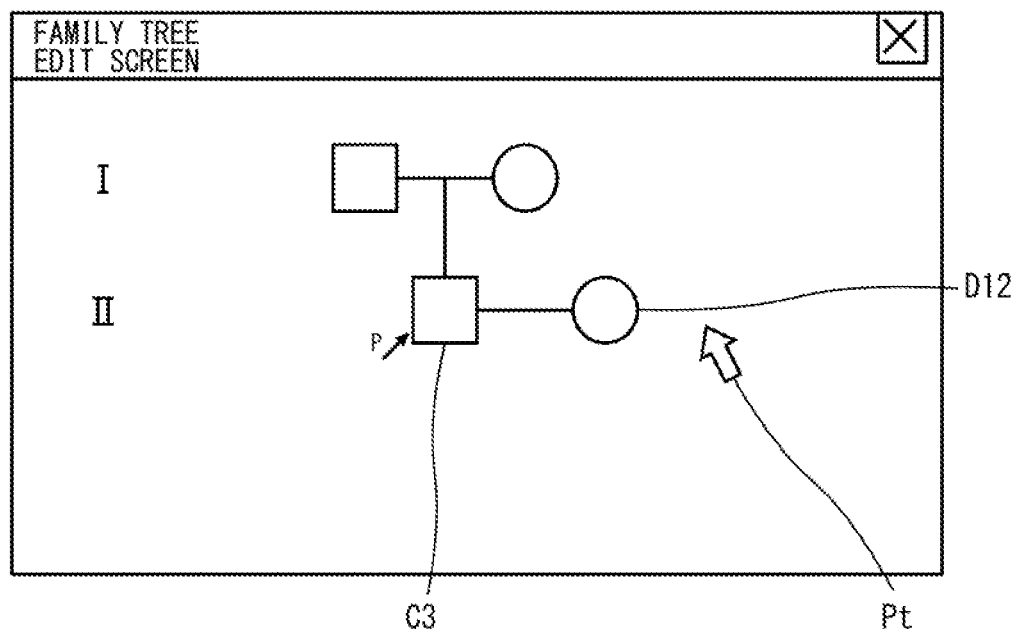

When the process of the step S207 is completed or skipped, the connection state display unit 208 displays the person symbol and the candidate person symbol while the person symbol is being connected with the candidate person symbol (step S208). More specifically, the connection state display unit 208 transmits information that causes the terminal device 100 to display the person symbol and the candidate person symbol while the person symbol is being connected with the candidate person symbol to the terminal device 100. This process causes the terminal device 100 to display the person symbol C3 and the candidate person symbol D12 while the person symbol C3 is being connected with the candidate person symbol D12 as illustrated in FIG. 15B.

Figure 16A:
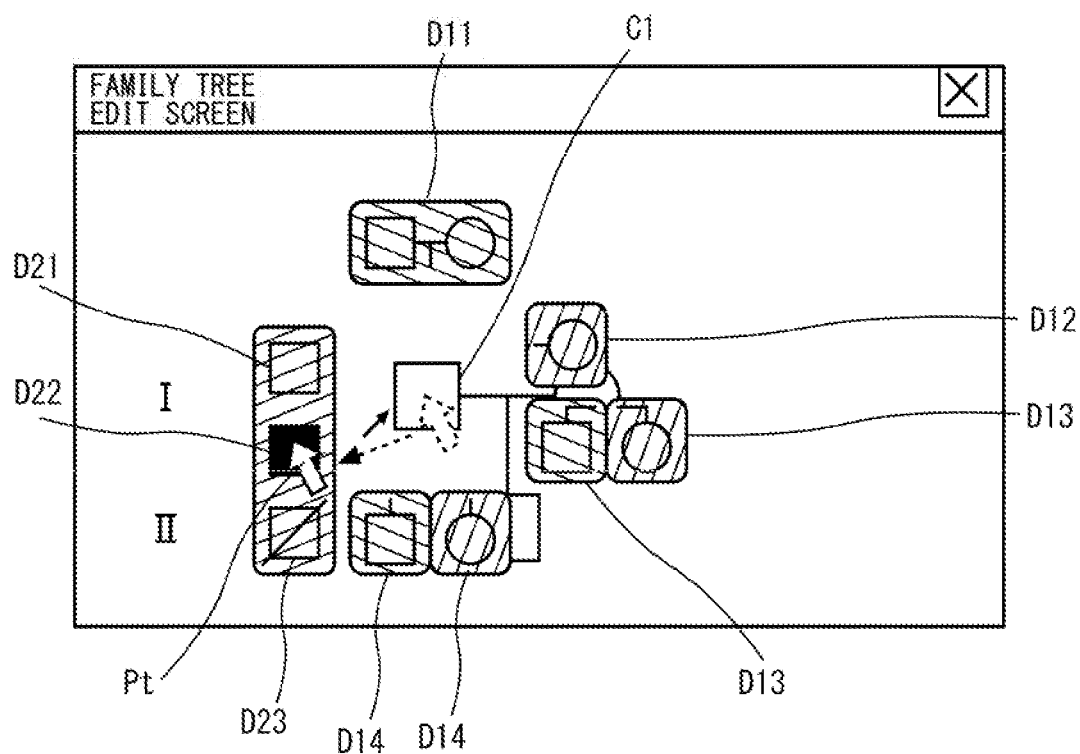
FIG. 16A and FIG. 16B illustrate other examples of the family tree edit screen.
Figure 16B:
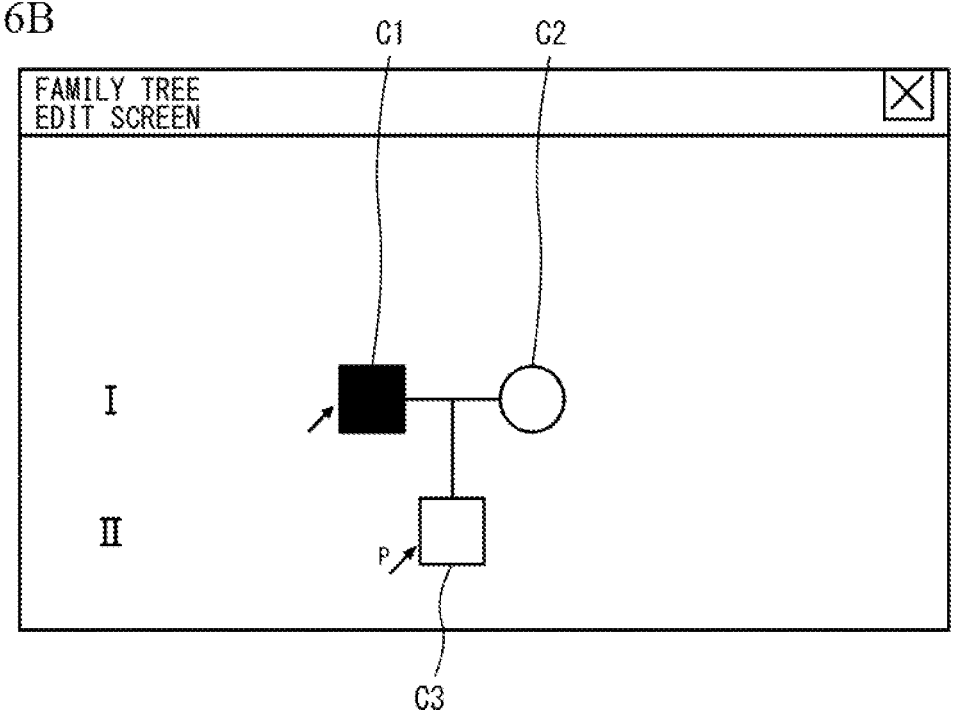

When the process of the step S208 is completed or when a connectable candidate person symbol was not selected at the step S204 (step S204: NO), the connection state display unit 208 determines whether the candidate person symbol for identifying the state of the person (hereinafter, referred to as a state-identifying candidate) has been selected (step S209). When determining that the state-identifying candidate has been selected (step S209: YES), the connection state display unit 208 changes the state of the person symbol to the state of the selected state-identifying candidate (step S210). For example, when the selecting operation (for example, a click) that selects the candidate person symbol D22 is conducted after the specifying operation that specifies the person symbol C1 has been conducted as illustrated in FIG. 16A, the terminal device 100 transmits the selecting operation including the candidate person symbol D22 to the server device 200. When the selecting operation reception unit 207 of the server device 200 receives the selecting operation transmitted from the terminal device 100, the connection state display unit 208 transmits information that changes the state of the person symbol C1 to the state of the selected candidate person symbol D22 to the terminal device 100. This process causes the terminal device 100 to change the state of the person symbol C1 to the state of the selected candidate person symbol D22 as illustrated in FIG. 16B.

On the other hand, when determining that the state-identifying candidate was not selected (step S209: NO), the connection state display unit 208 skips the process of the step S210. When the process of the step S210 is completed or skipped, the connection state display unit 208 ends the process.

Figure 17A:
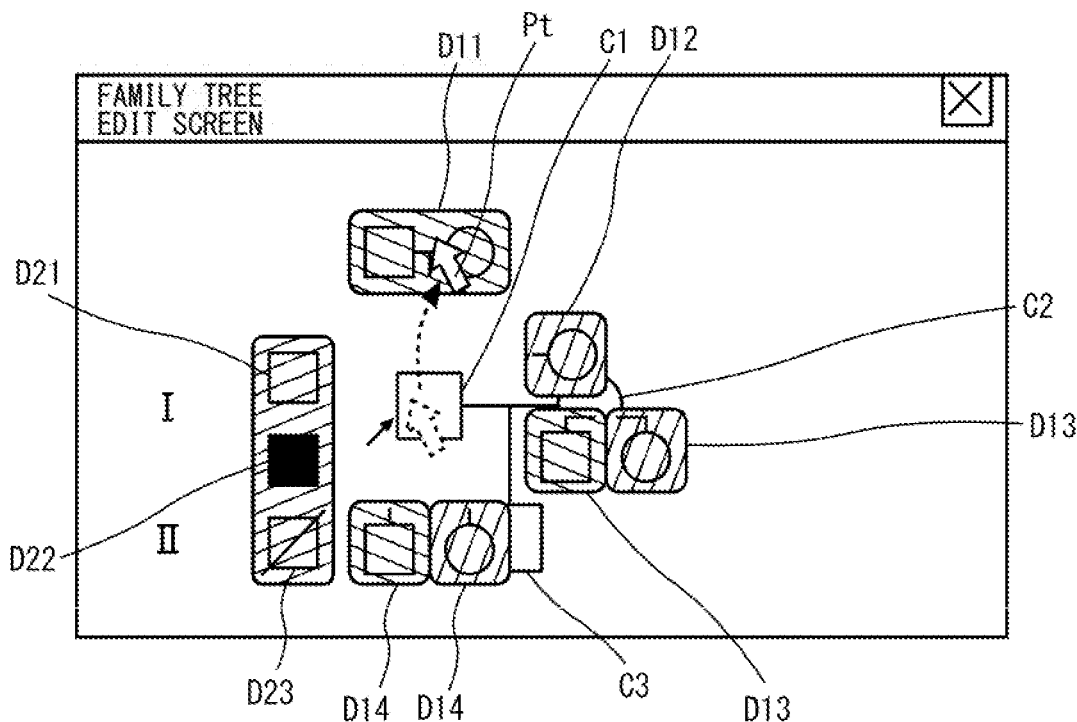
FIG. 17A and FIG. 17B illustrate other examples of the family tree edit screen.
Figure 17B:
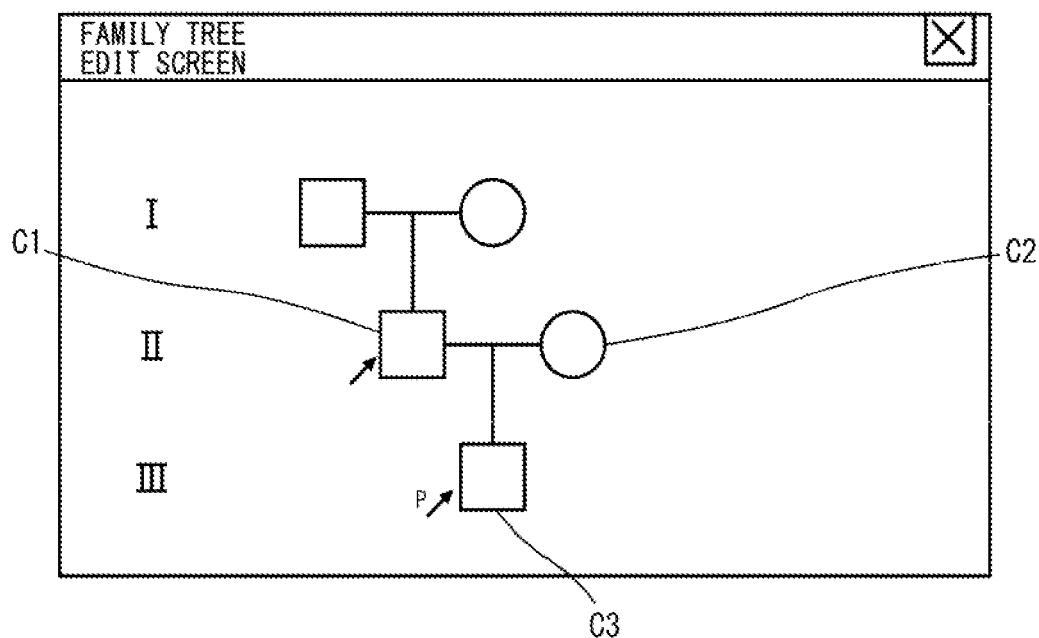

With reference to FIG. 17A and FIG. 17B, the change of the generation number executed in the process of the above step S207 will be described in detail.

For example, when the selecting operation (for example, a click) that selects the candidate person symbol D11 is conducted after the specifying operation that specifies the person symbol C1 has been conducted as illustrated in FIG. 17A, the terminal device 100 transmits the selecting operation including the candidate person symbol D11 to the server device 200. When the selecting operation reception unit 207 of the server device 200 receives the selecting operation transmitted from the terminal device 100, the connection state display unit 208 accesses the relationship information storage unit 202 and updates the relationship information of the parent-child relationship. Furthermore, when the selecting operation that selects the candidate person symbol D11 representing parents is conducted, the generation of the person symbol C1 that was subject to the specifying operation moves forward by one. Thus, the connection state display unit 208 changes the generation number, and transmits information that causes the terminal device 100 to display the changed generation number to the terminal device 100. This process causes the terminal device 100 to change the generation number of the person symbol C1 from the generation number "I" representing the first generation to the generation number "II" representing the second generation as illustrated in FIG. 17B. In the same manner, the terminal device 100 changes the generation number of the person symbol C3 from the generation number "II" representing the second generation to the generation number "III" representing the third generation.

A description will next be given of the display of the above determination condition with reference to FIG. 18 through FIG. 20B.

Figure 18:
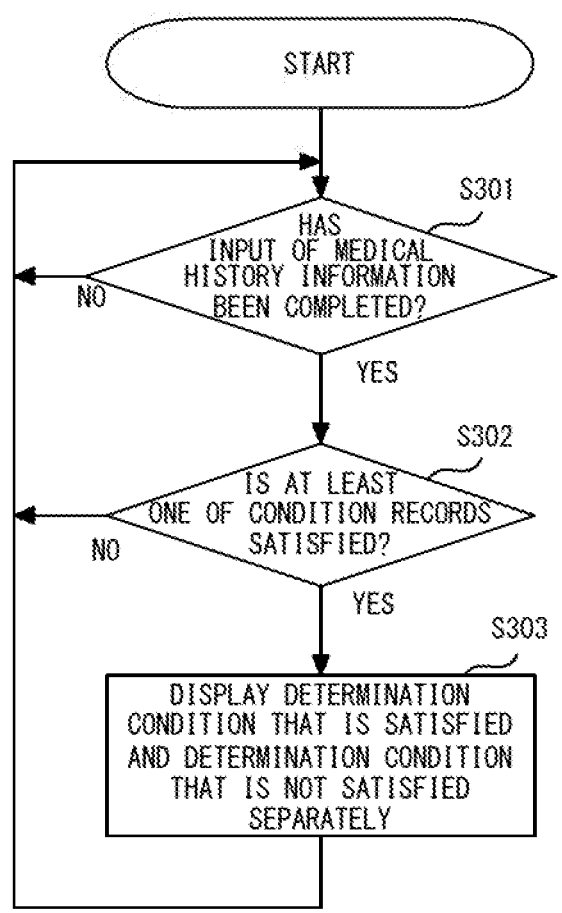
FIG. 18 is a flowchart of yet another exemplary operation of the server device.
Figure 19:
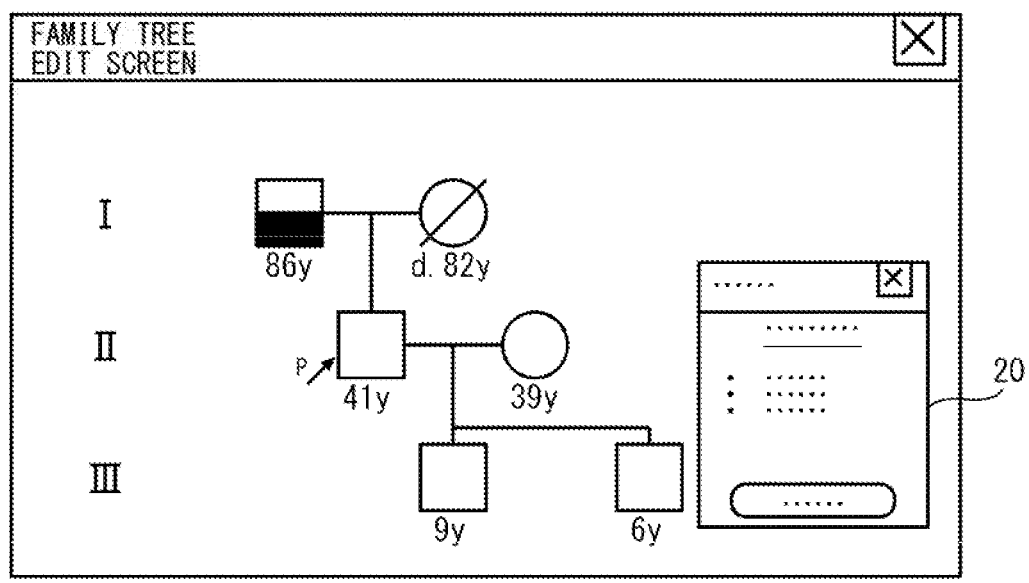
FIG. 19 illustrates another example of the family tree edit screen.
Figure 20A:
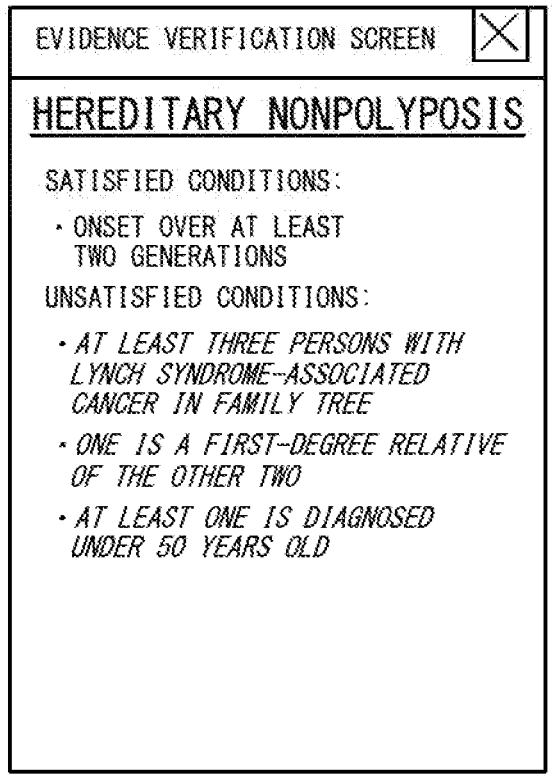
FIG. 20A illustrates an example of an evidence verification screen.
Figure 20B:
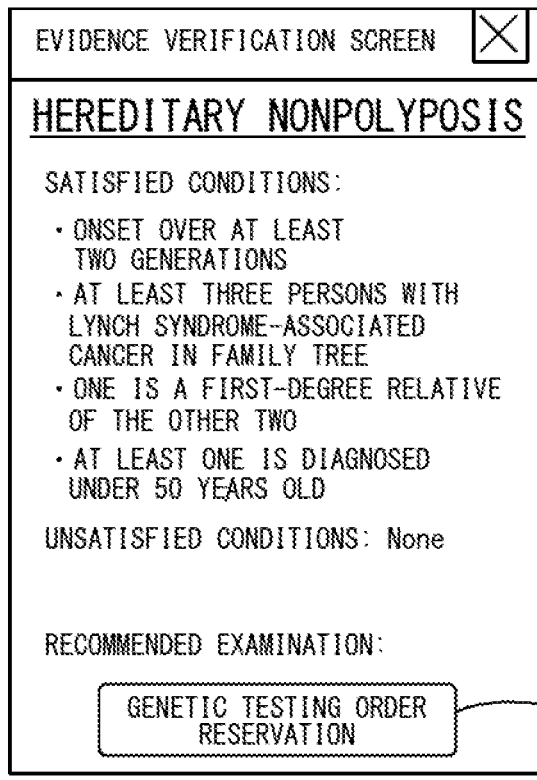
FIG. 20B illustrates another example of the evidence verification screen.

FIG. 18 is a flowchart of another exemplary operation of the server device 200. FIG. 19 illustrates another example of the family tree edit screen. FIG. 20A illustrates an evidence verification screen 20. FIG. 20B illustrates another example of the evidence verification screen 20.

As illustrated in FIG. 18, the connection candidate display unit 206 waits until the input of the medical history information is completed (step S301: NO). When the input of the medical history information has been completed (step S301: YES), the connection candidate display unit 206 determines whether at least one of the condition records of the condition information is satisfied (step S302). More specifically, when the input of the medical history information is completed, the terminal device 100 transmits the medical history information to the server device 200. When the specifying operation reception unit 205 of the server device 200 receives the medical history information transmitted from the terminal device 100, the connection candidate display unit 206 accesses the family tree information storage unit 201, the relationship information storage unit 202, the personal information storage unit 203, and the condition information storage unit 204 to obtain the family tree information, the relationship information, the personal information, and the condition information. When obtaining such various information, the connection candidate display unit 206 determines whether the medical history information received by the specifying operation reception unit 205 satisfies at least one of the determination conditions of the condition records in the condition information by using the family tree information, the relationship information, and the personal information.

When determining that none of the condition records is satisfied (step S302: NO), the connection candidate display unit 206 returns to the process of the step S301. On the other hand, when determining that at least one of the condition records is satisfied (step S302: YES), the connection state display unit 208 displays the condition record that is satisfied and the condition record that is not satisfied separately (step S303). More specifically, the connection state display unit 208 transmits information that causes the evidence verification screen including the determination conditions of the condition information to be displayed to the terminal device 100. This process causes the terminal device 100 to display the evidence verification screen 20 as illustrated in FIG. 19. The displayed position of the evidence verification screen 20 may be a position at which at least a part of the evidence verification screen 20 overlaps with the family tree edit screen, or a position at which the evidence verification screen 20 does not overlap at all. Upon completion of the processing of the step S303, the process returns to the step S301.

The evidence verification screen 20 is divided into an area for displaying satisfied conditions representing the determination conditions of the condition information that are satisfied and an area for displaying unsatisfied conditions representing determination conditions of the condition information that are not satisfied as illustrated in FIG. 20A and FIG. 20B. For example, as illustrated in FIG. 20A, when the medical history information satisfies at least one of the determination conditions, the determination condition that is satisfied is displayed in the area for displaying the satisfied conditions, and the determination condition that is not satisfied is displayed in the area for displaying the unsatisfied conditions. The doctor checks the determination conditions displayed in the part for displaying the unsatisfied conditions, and understands the contents to be collected next from the patient, the family member of the patient, or a consulter. Because the doctor checks the determination condition displayed in the area for displaying the unsatisfied conditions, the determination condition displayed in the area for displaying the satisfied condition may be made not to be displayed by control.

On the other hand, as illustrated in FIG. 20B, when the medical history information satisfies all the determination conditions, all the determination conditions that are satisfied are displayed in the area for displaying the satisfied conditions, and the determination condition that is not satisfied is not displayed in the area for displaying the unsatisfied conditions. In this case, when determining that the probability of the person developing a disease is equal to or greater than a predetermined value based on the past record information stored in the condition information storage unit 204, the connection state display unit 208 transmits information that causes information about an examination, which is to be recommended, to be displayed on the evidence verification screen 20 to the terminal device 100. This process causes the terminal device 100 to display the evidence verification screen 20 including the information about the examination to be recommended. Examples of the information about the examination to be recommended include a button 20a for making an examination reservation as illustrated in FIG. 20B.

As described above, in the present embodiment, the server device 200 includes the specifying operation reception unit 205, the connection candidate display unit 206, the selecting operation reception unit 207, and the connection state display unit 208. The specifying operation reception unit 205 receives a specifying operation that specifies a person symbol from person symbols representing persons present in a family tree. The connection candidate display unit 206 refers to the personal information storage unit 203 to display candidate person symbols capable of being connected with the person symbol specified by the specifying operation. The selecting operation reception unit 207 receives a selecting operation that selects a candidate person symbol from the candidate person symbols displayed by the connection candidate display unit 206. The connection state display unit 208 displays the candidate person symbol selected by the selecting operation received by the selecting operation reception unit 207 while the selected candidate person symbol is being connected with the person symbol specified by the specifying operation. This process reduces time and effort to construct a family tree. Especially, the use of symbols representing the connection relationship is omitted. Thus, the family tree is easily constructed. Additionally, the family tree is not dynamically constructed, after the attribute information for the person symbol is input, based on the input attribute information. The attribute information is linked to individual person symbols on the family tree while the family tree is being constructed according to the gathered contents. Thus, the gathered contents are instantly reflected on the family tree.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various change, substitutions, and alterations could be made hereto without departing from the spirit and scope of the invention. For example, the connection state display unit 208 may extract the family tree information of a family tree similar to the family tree that is subject to an operation from the family tree information storage unit 201 and display the family tree of the extracted family tree information. This configuration allows the doctor to understand the past course of treatment employed to a person in the similar family tree and the past procedures and employ an appropriate course of treatment.

What is claimed is:

1. A non-transitory computer-readable storage medium storing a family tree construction supporting program causing a computer to execute a process, the process comprising:

determining whether to receive a first operation or not that specifies a person symbol from a plurality of person symbols representing persons present in a family tree with symbols, the first operation being an operation that overlaps a position of a mouse pointer with the person symbol, the plurality of person symbols being based on nomenclature standardized by the American Society of Human Genetics;

when the first operation is received, displaying a plurality of first candidate person symbols capable of being connected with the person symbol specified by the received first operation by referring to a first storage unit that stores attribute information with respect to each of a plurality of persons, the plurality of first candidate person symbols being filtered and displayed based on the stored attribute information, the plurality of first candidate person symbols representing candidates of the plurality of person symbols and each of the plurality of the first candidate person symbols having a respective connector symbol that represents a connection relationship, one end of the respective connector symbol being not attached to the person symbol specified by the received first operation and the other end of the respective connector symbol being attached to the each of the plurality of the first candidate person symbols;

receiving a second operation that selects a first candidate person symbol from the plurality of first candidate person symbols that have been displayed, the second operation being an operation that selects the first candidate person symbol; and displaying the first candidate person symbol selected by the received second operation while the selected first candidate person symbol is being connected with the person symbol specified by the first operation by the one end of a connector symbol of the selected first candidate person symbol, wherein the plurality of first candidate person symbols are displayed at the same time when a state is changed from a first state where the position of the mouse pointer overlaps with none of the person symbols to a second state where the position of the mouse pointer overlaps with the person symbol.

2. The non-transitory computer-readable storage medium according to claim 1, wherein the process further comprises:
   displaying a plurality of second candidate person symbols for identifying a state of a person represented by the person symbol specified by the first operation together with the plurality of first candidate person symbols;
   receiving a third operation that selects a second candidate person symbol from the plurality of second candidate person symbols that have been displayed; and
   changing the person symbol specified by the first operation to the second candidate person symbol selected by the received third operation.

3. The non-transitory computer-readable storage medium according to claim 1, wherein the process further comprises:
   the displaying of the plurality of first candidate person symbols includes displaying a first candidate person symbol representing a parent, a first candidate person symbol representing a sibling, and a first candidate representing a child in different manners.

4. The non-transitory computer-readable storage medium according to claim 1, wherein the process further comprises:
   when receiving a fourth operation that requests to input medical history information of the person symbol, displaying a screen for inputting medical history information of a person represented by the person symbol that is subject to the received fourth operation; and
   changing a display mode of the person symbol that is subject to the fourth operation depending on a presence or absence of input of the medical history information.

5. The non-transitory computer-readable storage medium according to claim 4, wherein the process further comprises:
   changing a display mode of a person symbol in a manner that makes it recognizable that a plurality of sets of the medical history information are input when a plurality of sets of the medical history information have been input on the displayed screen.

6. The non-transitory computer-readable storage medium according to claim 1, wherein the process further comprising:
   referring to a second storage unit that stores information including a plurality of condition records for determining a genetic disease every time input of medical history information of a person present in the family tree is completed; and
   when the input medical history information satisfies at least one of the plurality of condition records, displaying at least a condition record that is not satisfied.

7. The non-transitory computer-readable storage medium according to claim 1, wherein the process further comprising:
   referring to a second storage unit that stores information including a plurality of condition records for determining a genetic disease and information about a past record of onset of the genetic disease in a family structure similar to a family structure present in the family tree every time input of medical history information of a person present in the family tree is completed; and
   when a probability of a person developing the genetic disease is equal to or greater than a predetermined value, displaying information about an examination to be recommended.

8. The non-transitory computer-readable storage medium according to claim 1, wherein the process further comprising:
   extracting family tree information of a family tree similar to the family tree that is subject to an operation from a third storage unit that stores a plurality of sets of the family tree information; and
   displaying a family tree of the extracted family tree information.

9. The non-transitory computer-readable storage medium according to claim 1, wherein the process further comprising:
   when the second operation is received and a generation number of each generation present in the family tree is changed, allocating a new number to the generation number and displaying the new generation number.

10. The non-transitory computer-readable storage medium according to claim 1, wherein the plurality of first candidate person symbols surround the person symbol specified by the received first operation.

11. A family tree construction supporting method implemented by a computer, the family tree construction supporting method comprising:
   determining whether to receive a first operation or not that specifies a person symbol from a plurality of person symbols representing persons present in a family tree with symbols, the first operation being an operation that overlaps a position of a mouse pointer with the person symbol, the plurality of person symbols being based on nomenclature standardized by the American Society of Human Genetics;
   when the first operation is received, displaying a plurality of first candidate person symbols capable of being connected with the person symbol specified by the received first operation by referring to a first storage unit that stores attribute information with respect to each of a plurality of persons, the plurality of first candidate person symbols being filtered and displayed based on the stored attribute information, the plurality of first candidate person symbols representing candidates of the plurality of person symbols and each of the plurality of the first candidate person symbols having a respective connector symbol that represents a connection relationship, one end of the respective connector symbol being not attached to the person symbol specified by the received first operation and the other end of the respective connector symbol being attached to the each of the plurality of the first candidate person symbols;
   receiving a second operation that selects a first candidate person symbol from the plurality of first candidate person symbols that have been displayed, the second operation being an operation that selects the first candidate person symbol; and
   displaying the first candidate person symbol selected by the received second operation while the selected first candidate person symbol is being connected with the person symbol specified by the first operation by the one end of a connector symbol of the selected first candidate person symbol,
   wherein the plurality of first candidate person symbols are displayed at the same time when a state is changed from a first state where the position of the mouse pointer overlaps with none of the person symbols to a second state where the position of the mouse pointer overlaps with the person symbol.

12. A family tree construction supporting device comprising:
a memory configured to store attribute information with respect to each of a plurality of persons; and
a processor coupled to the memory and configured to:
determine whether to receive a first operation or not that specifies a person symbol from a plurality of person symbols representing persons present in a family tree with symbols, the first operation being an operation that overlaps a position of a mouse pointer with the person symbol, the plurality of person symbols being based on nomenclature standardized by the American Society of Human Genetics;
when the first operation is received, display a plurality of first candidate person symbols capable of being coupled to the person symbol specified by the received first operation by referring to the memory, the plurality of first candidate person symbols being filtered and displayed based on the stored attribute information, the plurality of first candidate person symbols representing candidates of the plurality of person symbols and each of the plurality of the first candidate person symbols having a respective connector symbol that represents a connection relationship, one end of the respective connector symbol being not attached to the person symbol specified by the received first operation and the other end of the respective connector symbol being attached to the each of the plurality of the first candidate person symbols;
receive a second operation that selects a first candidate person symbol from the plurality of first candidate person symbols that have been displayed, the second operation being an operation that selects the first candidate person symbol; and
display the first candidate person symbol selected by the received second operation while the selected first candidate person symbol is being connected with the person symbol specified by the first operation by the one end of a connector symbol of the selected first candidate person symbol,
wherein the plurality of first candidate person symbols are displayed at the same time when a state is changed from a first state where the position of the mouse pointer overlaps with none of the person symbols to a second state where the position of the mouse pointer overlaps with the person symbol.

13. The family tree construction supporting device according to claim 12, wherein
the processor is configured to:
display a plurality of second candidate person symbols for identifying a state of a person represented by the person symbol specified by the first operation together with the plurality of first candidate person symbols;
receive a third operation that selects a second candidate person symbol from the plurality of second candidate person symbols that have been displayed; and
change the person symbol specified by the first operation to the second candidate person symbol selected by the received third operation.

14. The family tree construction supporting device according to claim 12, wherein
the processor is configured to display a first candidate person symbol representing a parent, a first candidate person symbol representing a sibling, and a first candidate person symbol representing a child in different manners when displaying the plurality of first candidate person symbols.

15. The family tree construction supporting device according to claim 12, wherein
the processor is configured to:
when receiving a fourth operation that requests to input medical history information of the person symbol, display a screen for inputting medical history information of a person represented by a person symbol that is subject to the received fourth operation; and
change a display mode of the person symbol that is subject to the fourth operation depending on a presence or absence of input of the medical history information.

16. The family tree construction supporting device according to claim 15, wherein
the processor is configured to:
when a plurality of sets of the medical history information have been input on the displayed screen, change a display mode of a person symbol in a manner that makes it recognizable that a plurality of sets of the medical history information are input.

17. The family tree construction supporting device according to claim 12, wherein
the memory is configured to store information including a plurality of condition records for determining a genetic disease, and
the processor is configured to:
refer to the memory every time input of medical history information of a person present in the family tree is completed; and
when the input medical history information satisfies at least one of the plurality of condition records, display at least a condition record that is not satisfied.

18. The family tree construction supporting device according to claim 12, wherein
the memory is configured to store information including a plurality of condition records for determining a genetic disease and information about a past record of onset of the genetic disease in a family structure similar to a family structure present in the family tree, and
the processor is configured to:
refer to the memory every time input of medical history information of a person present in the family tree is completed; and
when a probability of a person developing the genetic disease is equal to or greater than a predetermined value, display information about an examination to be recommended.

19. The family tree construction supporting device according to claim 12, wherein
the memory is configured to store a plurality of sets of family tree information, and
the processor is configured to:
extract the family tree information of a family tree similar to the family tree that is subject to an operation from the memory; and
display a family tree of the extracted family tree information.

20. The family tree construction supporting device according to claim 12, wherein
the processor is configured to, when the second operation is received and a generation number of each generation present in the family tree is changed, allocate a new number to the generation number and display the new generation number.

\* \* \* \* \*